(12) United States Patent
Gow et al.

(10) Patent No.: US 12,082,914 B2
(45) Date of Patent: *Sep. 10, 2024

(54) EVALUATION SYSTEM FOR CARDIOVASCULAR HEALTH ASSESSMENT AND INDIVIDUALIZED HEALTH AND FITNESS INTERVENTIONS

(71) Applicant: RUTGERS, THE STATE UNIVERSITY OF NEW JERSEY, New Brunswick, NJ (US)

(72) Inventors: Andrew J. Gow, Princeton, NJ (US); Gillian M. Cannon, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,425

(22) Filed: May 16, 2022

(65) Prior Publication Data
US 2022/0273179 A1    Sep. 1, 2022

Related U.S. Application Data

(63) Continuation of application No. 16/626,498, filed as application No. PCT/US2018/039581 on Jun. 26, 2018, now Pat. No. 11,330,986.
(Continued)

(51) Int. Cl.
*A61B 5/0205*    (2006.01)
*A61B 5/00*    (2006.01)
(Continued)

(52) U.S. Cl.
CPC ........ *A61B 5/0205* (2013.01); *A61B 5/02007* (2013.01); *A61B 5/026* (2013.01);
(Continued)

(58) Field of Classification Search
CPC ... A61B 5/0205; A61B 5/02007; A61B 5/026; A61B 5/4035; A61B 5/486; A61B 5/4884; A61B 5/024
See application file for complete search history.

(56) References Cited

U.S. PATENT DOCUMENTS

| | | |
|---|---|---|
| 9,402,597 B1 | 8/2016 | Castellanos |
| 10,610,113 B2 * | 4/2020 | Najarian .............. A61B 5/0295 |

(Continued)

FOREIGN PATENT DOCUMENTS

| | | |
|---|---|---|
| CN | 106539562 A | 3/2017 |
| CN | 106576183 A | 4/2017 |

OTHER PUBLICATIONS

International Search Report and Written Opinion issued in International Application No. PCT/US18/39581, mailed Sep. 24, 2018, 14 pages.
(Continued)

*Primary Examiner* — Carl H Layno
*Assistant Examiner* — Manolis Pahakis
(74) *Attorney, Agent, or Firm* — Talem IP Law, LLP

(57) ABSTRACT

A cardiovascular health assessment score, representing a working tissue flow and indicating the dependence on central and peripheral control mechanisms, is generated by an evaluation system and used to support a variety of individualized medicine and health applications. One or more of the individualized medicine and health applications may be implemented as part of the evaluation system and incorporate the cardiovascular health assessment.

12 Claims, 17 Drawing Sheets

Related U.S. Application Data

(60) Provisional application No. 62/525,967, filed on Jun. 28, 2017.

(51) Int. Cl.

| | | |
|---|---|---|
| *A61B 5/02* | (2006.01) | |
| *A61B 5/021* | (2006.01) | |
| *A61B 5/022* | (2006.01) | |
| *A61B 5/024* | (2006.01) | |
| *A61B 5/026* | (2006.01) | |
| *G16H 50/30* | (2018.01) | |

(52) U.S. Cl.
CPC ............ *A61B 5/4035* (2013.01); *A61B 5/486* (2013.01); *A61B 5/4884* (2013.01); *G16H 50/30* (2018.01); *A61B 5/02108* (2013.01); *A61B 5/02233* (2013.01); *A61B 5/024* (2013.01); *A61B 5/02416* (2013.01)

(56) References Cited

U.S. PATENT DOCUMENTS

| | | | |
|---|---|---|---|
| 2003/0040675 A1* | 2/2003 | Sharrock | A61B 5/02141 |
| | | | 600/490 |
| 2006/0178585 A1 | 8/2006 | Sharrock | |
| 2007/0225614 A1 | 9/2007 | Naghavi et al. | |
| 2010/0152547 A1* | 6/2010 | Sterling | A61B 5/029 |
| | | | 600/301 |
| 2010/0185220 A1 | 7/2010 | Naghavi et al. | |
| 2011/0172505 A1 | 7/2011 | Kim et al. | |
| 2012/0065514 A1 | 3/2012 | Naghavi et al. | |
| 2013/0053655 A1 | 2/2013 | Castellanos | |
| 2013/0267858 A1* | 10/2013 | Berkow | A61B 5/7278 |
| | | | 600/479 |
| 2015/0335288 A1* | 11/2015 | Toth | A61B 5/6833 |
| | | | 600/391 |
| 2017/0013284 A1 | 1/2017 | Murakami | |
| 2017/0132384 A1 | 5/2017 | Park et al. | |
| 2017/0231490 A1* | 8/2017 | Toth | G16H 40/63 |
| | | | 600/558 |
| 2019/0175035 A1* | 6/2019 | Van Der Horst | A61B 8/145 |

OTHER PUBLICATIONS

Bombardini,Tonino et al "Cardiac reflections and natural vibrations: Force-frequency relation recording system in the stress echo lab", Cardiovascular Ultrasound, Nov. 22, 2007, 17 pages, vol. 5, No. 42, Biomed Central, London GB.

Nikolic, Sonja B et al: "Association of von Willebrand factor blood levels with exercise hypertension", European Journal of Applied Physiology, Dec. 25, 2014, pp. 1057-1065, vol. 115, No. 5, Springer Verlag, Heidelberg, DE.

Extended European Search Report issued in European Application No. 18822795.3, mailed Mar. 18, 2021, 11 pages.

First Office Action issued in Chinese Application No. 201880053722.X, Mailed Dec. 27, 2021, 19 Pages.

Non-Final Office Action issued in U.S. Appl. No. 16/626,498, mailed Jun. 28, 2021, 25 pages.

\* cited by examiner

EVALUATION SYSTEM FOR CARDIOVASCULAR HEALTH ASSESSMENT AND INDIVIDUALIZED HEALTH AND FITNESS INTERVENTIONS

CROSS-REFERENCE TO RELATED APPLICATION

This application is a continuation application of Ser. No. 16/626,498, filed Dec. 24, 2019, which issued as U.S. Pat. No. 11,330,986, which is the U.S. National Stage entry of PCT/US2018/039581, filed Jun. 26, 2018, which claims the benefit of U.S. Provisional Patent Application Ser. No. 62/525,967, filed Jun. 28, 2017.

BACKGROUND

Traditional screening for cardiovascular health relies on measures of central cardiac function; namely blood pressure, resting heart rate, and sometimes a stress test. In patients at risk for peripheral artery disease, such as diabetics, there are available a number of measures of endothelial function, including reactive hyperemia tests and pulse wave analysis. However, centralized and peripheral measures are usually considered independently and may not provide a full picture of how a person will respond to treatments and regimens, including dietary and other interventions.

BRIEF SUMMARY

An evaluation system for cardiovascular health assessment that can be used to tailor individualized interventions for the improvement of cardiovascular health is provided. An evaluation system can be implemented on a local computer or as a server that supports the evaluation system as a service. A cardiovascular health assessment score, representing a working tissue flow and indicating the dependence on central and peripheral control mechanisms, is generated by the evaluation system and used to support a variety of individualized medicine and health applications. One or more of the individualized medicine and health applications may be implemented as part of the evaluation system and incorporate the cardiovascular health assessment.

Instructions for performing a cardiovascular health assessment that are stored in memory storage of an evaluation system can be executed by a hardware processor of the evaluation system. The cardiovascular health assessment, when executed by the hardware processor of the evaluation system, determines a working tissue flow of a subject, including the relative peripheral control of the working tissue flow. The working tissue flow and the relative peripheral control of the working tissue flow can then be used to generate individualized interventions for that subject. The individualized interventions are based on the working tissue flow information regarding the extent that the subject is peripherally limited or centrally limited and particular objectives for that subject. For example, the working tissue flow can be directly output to a user interface of the system and/or used to tailor an individualized-to-the-subject regimen, including nutrition and/or other intervention as part of individualized medicine and health applications. The individualized interventions can be tailored not only to one assessment, but also reassessments taken over time, which may be used to adjust and/or generate further interventions.

In one implementation, the cardiovascular health assessment uses a measured total blood drive that represents a force on blood to pass through a vessel bed of a subject; a stiffness index representing stiffness of arterial structure of the subject; a local dilation response representing a hypoxic drive for dilation of a tissue of the subject; and an autonomic constriction index representing constriction of the vessel bed of the subject. Using the stiffness index, the local dilation response, and the autonomic constriction index, the system, when executing the instructions for performing the cardiovascular health assessment, can determine a value indicative of a resistance in the vessel bed of the subject, and then can determine a working tissue flow of the subject by dividing the measured total blood drive with the value indicative of the resistance in the vessel bed of the subject. One or more measurements used for an assessment can be updated and used to generate partial reassessments, which can be further used to track and/or monitor interventions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
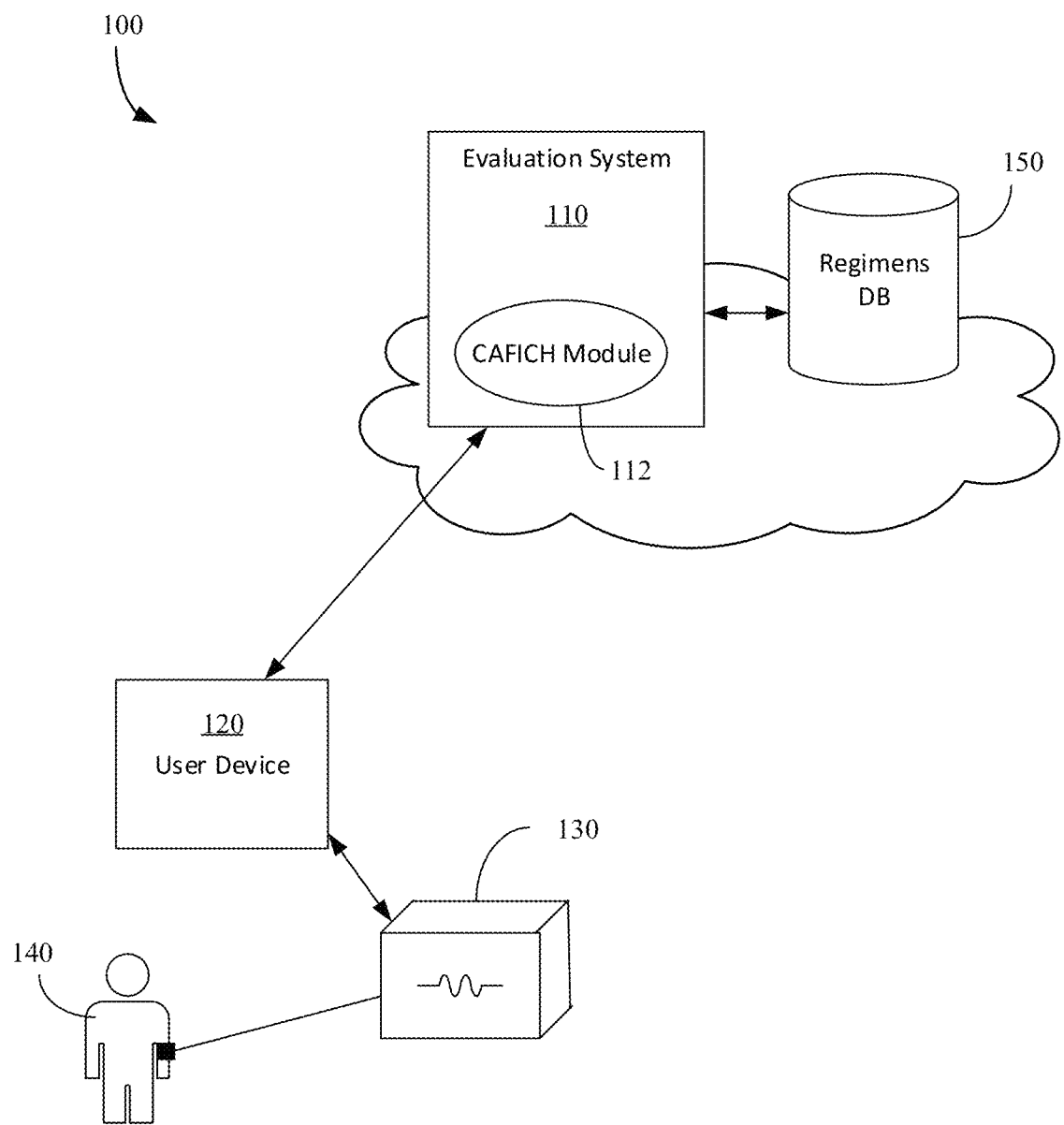
FIG. 1A illustrates an example operating environment.

An evaluation system for cardiovascular health assessment that can be used to tailor individualized interventions for the improvement of cardiovascular health is provided. As used herein, cardiovascular health refers to health or fitness.

Cardiovascular health is important for athletic performance as well as the diagnosis, treatment, and prevention of disease.

It is discovered that a real issue for both patients and athletes, is neither cardiac output (a central measure) nor endothelial responsiveness (a peripheral measure), but, rather, is blood flow to the working tissue. Targeted working tissue blood flow is critical to maintain adequate delivery of nutrients and removal of waste products, and both central and peripheral mechanisms are important in determining tissue blood flow.

The described systems determine working tissue blood flow through a combination of traditional central and peripheral measures of cardiovascular function; and can provide a completely new way of assessing, at the physiological level, if and how an individual is limited in blood flow delivery to the muscles/organs.

The inability to combine and identify relative contributions of these central and peripheral measures by other cardiovascular assessments can result in the implementation of interventions that are either not optimal, or in some cases, detrimental to the individual. Specifically, there are a number of both lifestyle and pharmacological approaches that can be used to improve tissue blood flow. Many people believe any of these approaches could work to address a subject's tissue blood flow; however, for many of these approaches some subjects are non-responsive. The described evaluation system and techniques can identify the cause of such perceived "non-responsiveness" and allow for targeting of more effective regimens.

Accordingly, the described evaluation system and techniques can be leveraged to make predictions regarding how an individual will respond to interventions.

For example, if today one was to go to the doctor's office and be diagnosed with hypertension, an initial pharmacological response may be to prescribe a beta-blocker. These drugs have been very successful at the population level; however, it has also been noted that there is enormous variability within individuals. Some of this variability can be attributed to differential pharmacokinetics as a result of patient genotype in genes as different as the cytochrome p450 enzymes and the adrenergic receptors. However, even armed with extensive genotyping one cannot predict what an individual's response to treatment will be. This means that often drugs are prescribed that initially have minimal beneficial effect. Being able to readily detect responsiveness can avoid or reduce delay in finding an effective prescription. A person's blood flow is determined by their genetics as well as by the effects of their lifestyle and environmental exposures. A challenge is that one needs to measure what a subject actually is, rather than what their genes predict them to be or what a diagnostic test defines their disease state as. For instance, an individual who is diagnosed with high blood pressure following routine exam and who has the appropriate genetic profile for treatment with metoprolol may have a minimal response to the drug as metoprolol corrects Cardiac Output (CO) but does not affect Total Peripheral Resistance (TPR), which may have been the cause of the diagnosis. By assessing Working Tissue Flow (WF) (and the relative peripheral control thereof) as presented herein, it can be possible to predict the physiological outcome of the treatment and thus administer and/or design better therapy.

In addition to predicting how an individual will respond to interventions, the described evaluation system and techniques can learn from accumulated data for adaptation to a test population (e.g., athletes or cardiovascular patients). The particular equation (and any weights and/or additional variables) calculated by the evaluation system to generate the relative peripheral control of the working tissue flow (and/or the working tissue flow itself) can depend on the therapeutic area or status of individuals. It is further possible to include values taken at different workloads to gain information concerning relative changes (e.g., the rates of increase in values such as local dilation as a function of workload).

FIG. 1A illustrates an example operating environment. Referring to FIG. 1A, an operating environment 100 can include an evaluation system 110, user device 120, and data collection system 130. In the implementation illustrated in FIG. 1A, the evaluation system 110 can be implemented as a server that supports the system as a service by communicating over a network with the user device 120 to obtain appropriate data about a subject 140 and output results.

The network can be, but is not limited to, a cellular network (e.g., wireless phone), a point-to-point dial up connection, a satellite network, the Internet, a local area network (LAN), a wide area network (WAN), a Wi-Fi network, an ad hoc network or a combination thereof. Indeed, the network may include one or more connected networks (e.g., a multi-network environment) including public networks, such as the Internet, and/or private networks such as a secure enterprise private network. Access to the network may be provided via one or more wired or wireless access networks as will be understood by those skilled in the art.

Figure 8:
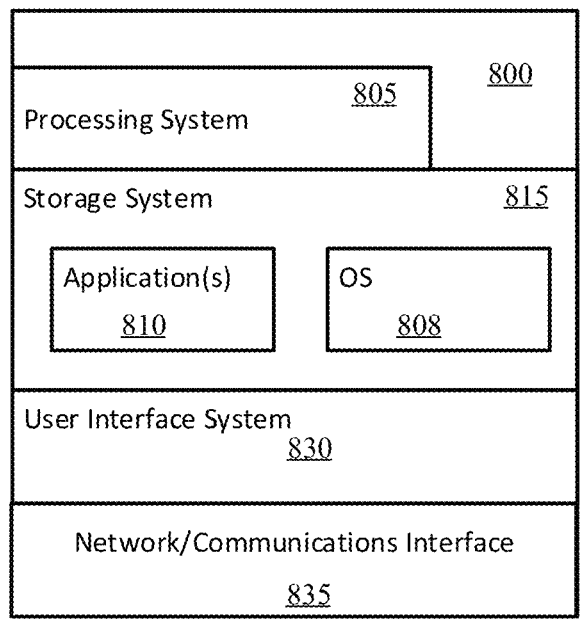
FIG. 8 shows a block diagram illustrating components of a computing device that may implement or communicate with an evaluation system.
Figure 9:
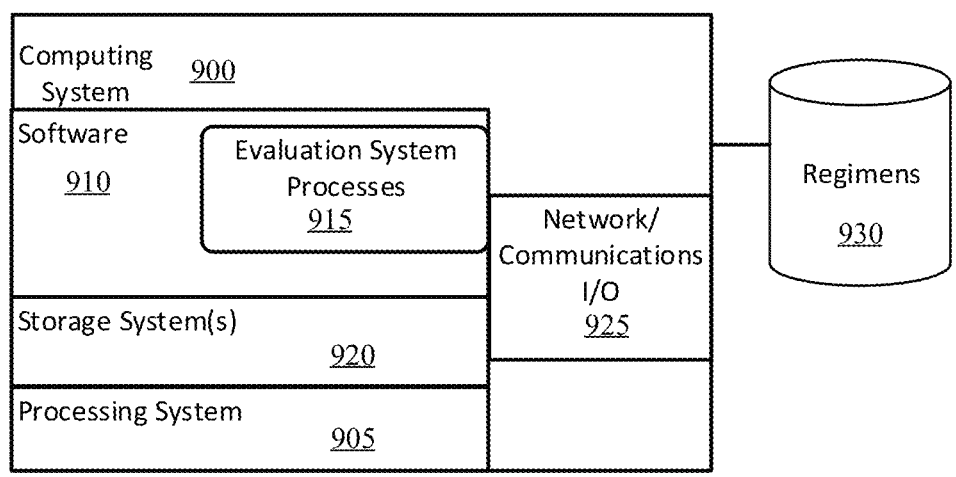
FIG. 9 illustrates a block diagram of a computing system that may implement the evaluation system as a service platform.

The evaluation system 110 may be embodied as computing system 900 such as described with respect to FIG. 9. In some cases, the evaluation system 110 can be implemented on a local computer (e.g., at user device 120, which can be embodied as computing system 800 such as described with respect to FIG. 8). In some cases, the evaluation system 110 can be implemented on a local computer, which can be integrated with or in communication with a medical instrument, and, therefore, be considered part of the data collection system 130.

In many implementations, evaluation system 110 includes one or more hardware processors and one or more storage media. Instructions for performing a cardiovascular health assessment can be stored in memory storage of the evaluation system 110 (e.g., as CAFICH module 112) and executed by a hardware processor of the evaluation system 110 to perform the cardiovascular health assessment. A cardiovascular health assessment score, representing a working tissue flow and indicating the dependence on central and peripheral control mechanisms, is generated by the CAFICH module 112 and used to support a variety of individualized medicine and health applications. One or more of the individualized medicine and health applications may be implemented as part of the evaluation system 110 and incorporate the cardiovascular health assessment (e.g., CAFICH module 112). The individualized medicine or health application can access health and fitness regimens 150 stored in memory storage of the evaluation system or at a remote location in order to identify and provide an appropriate health and fitness regimen (or other intervention plan). Of course, a practitioner can identify and prescribe appropriate health and fitness regimens that are not stored in the memory storage.

For example, a subject's health-related information (e.g., collected from data collection system 130 and/or input to device 120) can be input to the evaluation system 110. The evaluation system can then generate a health assessment score representing a relative peripheral control of the working tissue flow for the subject 140. The health assessment score is a value indicating where on a spectrum from cardiac limited to vascular limited that the subject's working tissue flow lies and the dependence of that flow on both central and peripheral factors. The cardiovascular health assessment score can then be used to identify a recommended routine for the individual. The individualized interventions are based on the working tissue flow information regarding the extent that the subject is peripherally limited or centrally limited and particular objectives for that subject. For example, the working tissue flow can be directly output to a user interface of the system and/or used, with the relative peripheral control of the working tissue flow, to tailor an individualized-to-the-subject regimen, including nutrition and/or other intervention as part of individualized medicine and health applications.

In addition to providing a current cardiovascular health assessment score, the subject's health assessment score can be tracked over time.

The subject's health-related information used by an evaluation system such as evaluation system 110 can include, but is not limited to, a total blood drive measurement, arterial stiffness measurement (the difference in time between the systolic peak and the reflection wave from a plethysmograph measurement of a peripheral artery, normalized for the size of the individual), reactive hyperemia index (and/or local dilation response), an autonomic constriction index, height, weight, body fat percentage, hydration level, and baseline heart rate.

Data collection of central and peripheral measures of cardiovascular function from the subject 140 may be carried out using multiple devices and sensors. In some cases, the data collection system 130 is part of, or communicates with, the user device 120. In addition to the sensor measurements collected by the data collection system 130, body weight, age, and other biometric or subject characteristic or identifier can be collected as part of the data collection. The information may be directly input by a user of the user device 120 or obtained via any suitable means (e.g., with permission from a subject's health records stored locally or remotely from the device 120). In some cases, aspects of the evaluation system can be incorporated in a machine that performs the data collection (e.g., integrated with, or in communication with, a medical instrument). Indeed, features of the evaluation system 110, user device 120, and data collection system 130 may be integrated into a single machine.

In some cases, where not all data is available, the evaluation system may still be able to perform a preliminary cardiovascular health assessment using assumed or estimated measurements. For example, the stiffness index, the local dilation response, and the autonomic constriction index can all be calculated or estimated by using pulse wave pressure analysis (and change in pulse wave pressure relative to exercise). In some cases, said measurements can be taken by a user at the gym, for example, when wearing a fitness tracker or other wearable device.

After at least an initial CAFICH score is generated for an individual, that score may be reassessed upon receipt of at least one updated measure. For example, the described evaluation system can include an application interface (e.g., a suitable application programming interface (API)) through which fitness trackers or other measurement devices can communicate updated measurements and, in some cases, have updated assessment scores (e.g., partial reassessment scores), after evaluation by the evaluation system, provided to the individual (directly for display or to be incorporated in a fitness or health intervention) or a designated party.

Figure 1B:
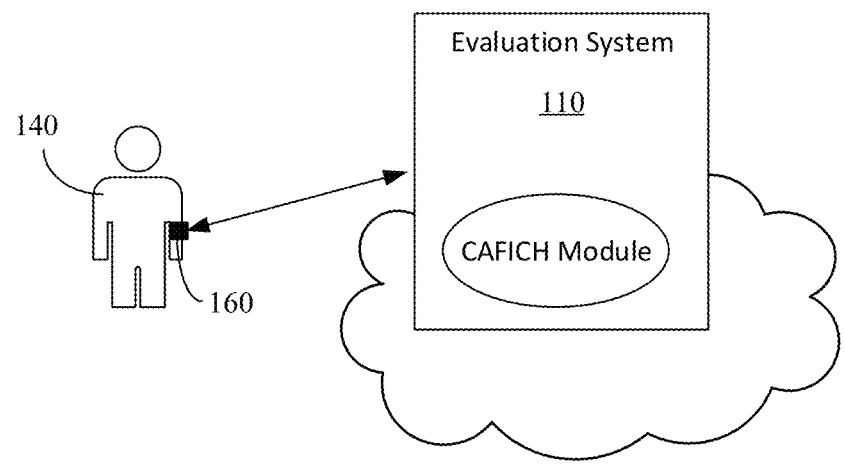
FIG. 1B illustrates an example tracker environment.

FIG. 1B illustrates an example tracker environment. Referring to FIG. 1B, subject 140 can use a wearable device 160 to collect data for regular, periodic, ad hoc, or otherwise-specified-by-user evaluation by the evaluation system 110. In some cases, wearable device 160 may include one or more of the components described with respect to computing device 800 of FIG. 8.

The evaluation system 110 can perform the reassessment using the updated measure obtained from the wearable device 160 and, for the remaining measures, the evaluation system 110 can use the previously obtained measures to generate a health assessment score representing a relative peripheral control of the working tissue flow for the subject 140.

In some cases, the wearable device 160 can support continuous assessment of responses that can be used to update the CAFICH score without requiring the running of the full battery of tests. For example, it is possible to measure pulse pressure waves through a number of wrist or finger based pressure devices. One or more of these devices can be used to measure the pulse wave shape and reflection notch rate as well as the initiation of systole. These parameters can be used to update a working tissue flow and relative peripheral control of the working tissue flow, for example, by recalculating a CAFICH score. In some cases, a piezo-electrode plaster on a subject's neck can be used to measure carotid pulse response. Said recording can be used in conjunction with wrist measurements to calculate an augmentation index that can effectively track the relative speed of blood flow. The calculation of the relative speed of blood flow can be performed by one or more processors on the wearable device 160 or the separate measurements communicated to another computing device for processing (either after collection at the wearable or separately from the wearable and the neck plaster device). The relative speed of blood flow measurement can be incorporated into the determination of working tissue flow to provide updated measures and, when the wearable is, for example, a fitness tracker, an exercise response variable.

Fitness trackers or other trackers can provide the information back to the user/wearer as part of the fitness application running on or associated with the tracker (and as permitted by the user).

FIGS. 2A-2D illustrate example processes for performing a cardiovascular health assessment. These processes illustrate certain preliminary processes that are performed prior to, and often as a prerequisite for, generating a health assessment score. As mentioned above, the evaluation system generates a health assessment score representing working tissue flow and indicating the dependence on central and peripheral control mechanisms. Working Tissue Flow can be determined, for example, from central output, arterial stiffness, hypoxic drive for dilation, and autonomic (or central) drive for constriction. Obtaining these measures are described in more detail as follows.

Figure 2A:
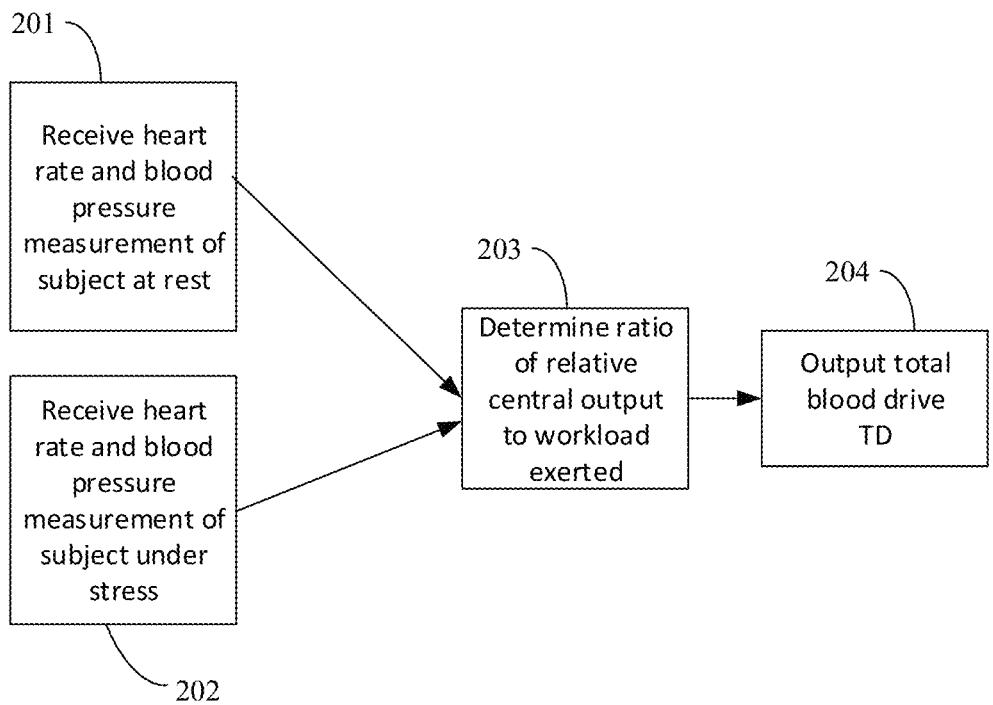
FIGS. 2A-2D illustrate example processes for performing a cardiovascular health assessment.

Referring to FIG. 2A, central output (CO) is a central measure that can readily be assessed from simple biometrics outputs, namely, height, weight, body fat percentage, hydration level, and baseline heart rate and blood pressure and hemoglobin saturation (e.g., obtained from a pulse oximeter). Using these measures, one can make assessments based on the Fick principle. For example, measuring the heart rate and blood pressure at rest gives the bottom end of CO, while measuring those same parameters (along with biometrics) under exercise or other stress allows one to assess maximal output. In this way, by monitoring heart rate during an exercise stress test, one can calculate the relative CO to workload exerted. Accordingly, a system that receives (201) heart rate and blood pressure measurements of a subject at rest and receives (202) heart rate and blood pressure measurements of the subject under stress can determine (203) a ratio of relative central output to workload exerted and output (204) total blood drive (TD). TD represents a force on blood to pass through a vessel bed of a subject.

Figure 3:
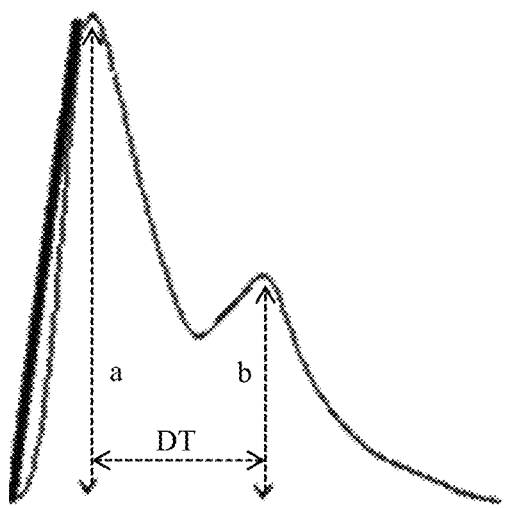
FIG. 3 shows a plot of a sample pulse wave.
Figure 2B:
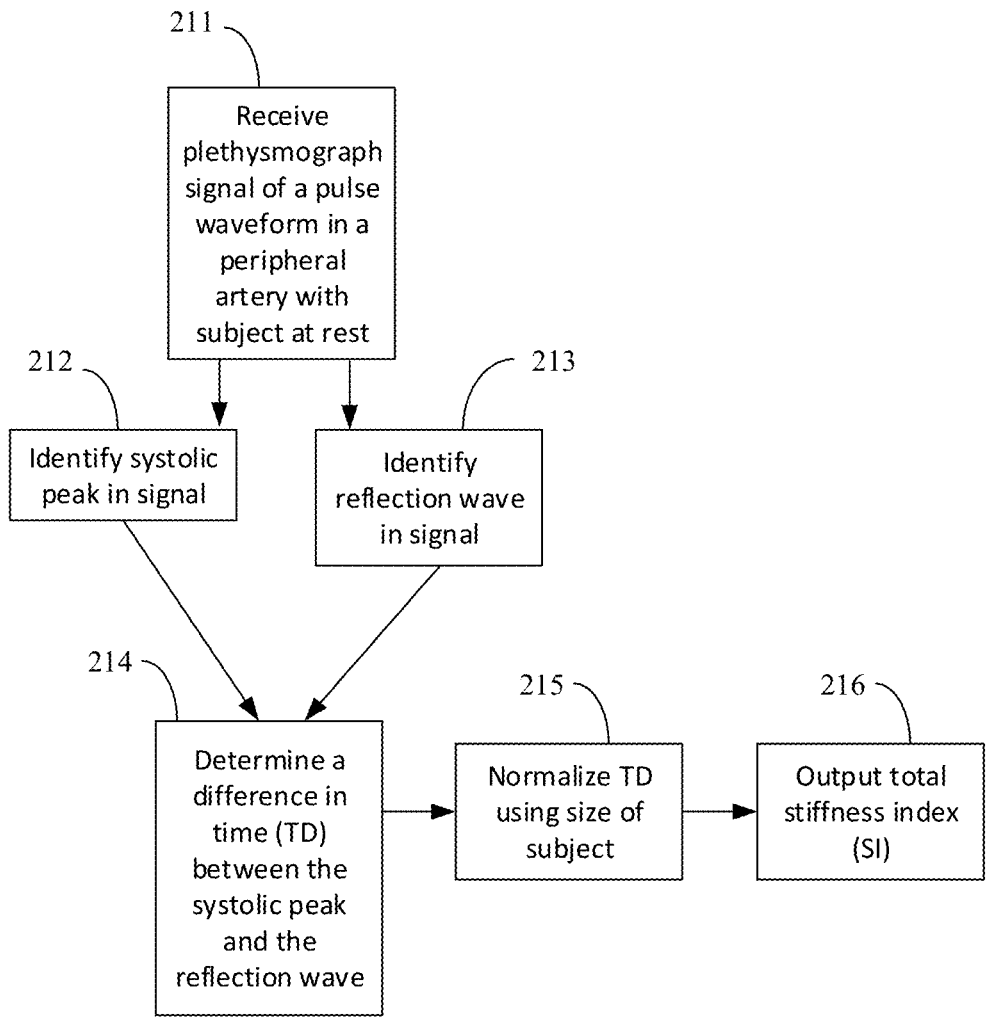

Referring to FIG. 2B, arterial stiffness can be identified because individuals have an inherent stiffness to their arterial structure, which is determined by basal smooth muscle tone and elastic structure. In one implementation, this peripheral measure can be measured at rest using a plethysmograph. Briefly, a plethysmograph allows one to measure the pulse waveform in a peripheral artery (see FIG. 3, which shows a plot of a sample pulse wave). As shown in FIG. 3, within this wave there is a systolic peak (a) and then a reflection (b) of that flow through the arterial system that is determined by the physical nature of the vessels. The difference in time (DT) between the systolic peak (a) and the reflection wave (b) is determined by arterial stiffness (which is also affected by the size of the individual). Accordingly, a system that receives (211) a plethysmograph signal with a pulse waveform in a peripheral artery can, after identifying (212) a systolic peak and identifying (213) a reflection wave in the signal, determine (214) a difference in time between the systolic peak and the reflection wave, normalize (215) the difference value for the size (e.g., height) of the individual by dividing a height of the patient by the difference in time, and output (216) the result as a stiffness index (SI). The plethysmograph may be implemented using a fitness tracker (e.g., a watch with appropriate sensors). In addition, as briefly mentioned above, pulse wave pressure analysis on the subject can not only be conducted to generate the SI, but also provide estimates for local dilation and autonomic constriction.

In another implementation, the stiffness index can be generated using brachial and central pulse pressure waves measured using a sphygmomanometer. The change in height over time can be assessed. For example, the brachial waveform can reflect the stiffness based on a presence or absence of a notch in the waveform on its falling edge. In addition, the rising edge at the systolic wave can impart information (e.g., based on the rise in pressure at the initiation of the systolic wave). Both features are reflected in the central pressure wave, for example, in the length of time (e.g., delay) to systolic peak and whether the waveform flattens or overshoots into diastole.

Figure 2C:
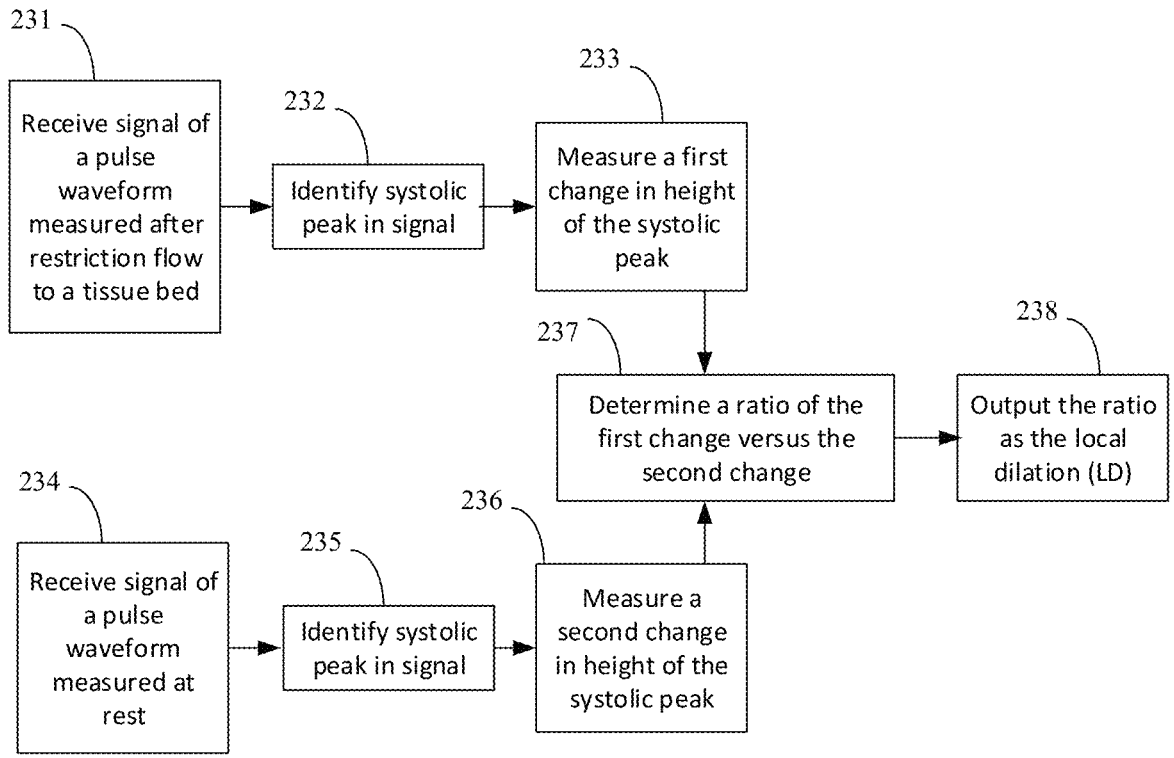

Referring to FIG. 2C, with reference to hypoxic drive for dilation, there are a number of factors that can drive a blood vessel to dilate. Many of these factors derive from local factors. The principle mechanism here is endothelial release of nitric oxide to relax smooth muscle and allow for vessel dilation and increased flow. One of the easiest measures of this peripheral measure is the capacity of an individual to increase local control of endothelium-mediated vasodilation, which is referred to as reactive hyperemia. Thus, this measure may also be referred to as the reactive hyperemia index (RHI). RHI is the ratio of test versus control arm vasodilation and is thus affected by autonomic output and stress within the test. By restricting flow to a tissue bed (such as forearm blood pressure cuff occlusion) one can monitor local flow. The consequent increase in flow post release of the restriction is entirely driven by local forces. This enables one to use the change in test arm amplitude as a measure of the local dilation (LD).

Accordingly, as illustrated in FIG. 2C, a system can generate a local dilation response by, after receiving (231) a signal of a pulse waveform measured after restriction of flow to a tissue bed and identifying (232) systolic peaks in the signal, measuring (233) a first change in a height of a systolic peak in a pulse; and, after receiving (234) a signal of a pulse waveform measured without first restricting flow to the tissue bed and identifying (235) systolic peaks in that signal, measuring (236) a second change in the height of the systolic peak, determining (237) a ratio of the measurement of the first change versus the measurement of the second change and outputting (238) the ratio as the local dilation LD. A forearm pressure cuff is used to restrict blood flow and a plethysmograph measurement is used to measure the Local Dilation (LD) response. As mentioned above, the plethysmograph may be implemented using a fitness tracker (e.g., a watch with appropriate sensors) and an estimate of LD generated from pulse wave pressure analysis.

Figure 2D:
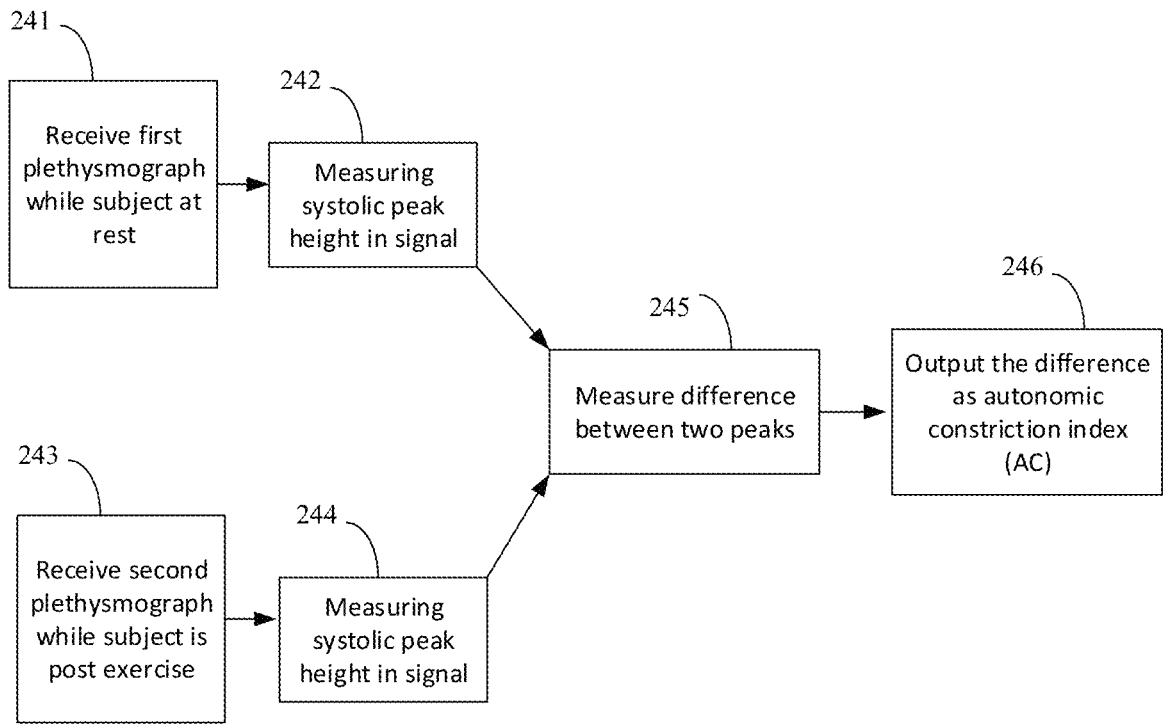

Referring to FIG. 2D, for autonomic (or central) drive for constriction, the autonomic nervous system attempts to maintain pressure in the face of increased metabolic demand by releasing factors, such as epinephrine, that cause smooth constriction and reduce blood flow. One of the stimuli that induce this constriction is maximal exercise. One can use pulse wave analysis once again comparing systolic peak height between rest and post exercise to assess this constriction. (It should be noted that in this test it is important that the measured vascular bed is not the working one). Accordingly, a system can generate the autonomic constriction index by receiving (241) first plethysmograph measurement taken when the subject was at rest, measuring (242) the systolic peak height of the first plethysmograph, receiving (243) a second plethysmograph measurement taken post exercise, measuring (244) the systolic peak height of the second plethysmograph, measuring (245) a difference between systolic peak height of the first plethysmograph and a second plethysmograph measurement taken post exercise, and outputting (246) the difference as the autonomic constriction index (AC). As described, a plethysmograph measurement can be taken for determining AC. The measurement can be made after cycle ergometry to generate an autonomic constriction index (AC) for the patient. As mentioned above, the plethysmograph may be implemented using a fitness tracker (e.g., a watch with appropriate sensors) and an estimate of AC generated from pulse wave pressure analysis.

These parameters can be obtained by the user, a medical professional or other practitioner and provided via some input mechanism to the evaluation system. For example, a practitioner can perform a patient cardiovascular stress test to measure total blood drive (TD). In some cases, an estimate or assumption for TD is used to generate a preliminary cardiovascular health assessment, which can be used by non-practitioner users as a screening for further assessment and/or to be directed to healthcare, or nutrition or fitness providers or regimens.

The practitioner can also perform a plethysmograph measurement to determine the arterial stiffness in a patient. The measurement determines the DT, which is based on the difference in time between the systolic peak and the reflection wave. The DT is normalized to yield the Stiffness Index ("SI")=(height/DT)).

Figure 4:
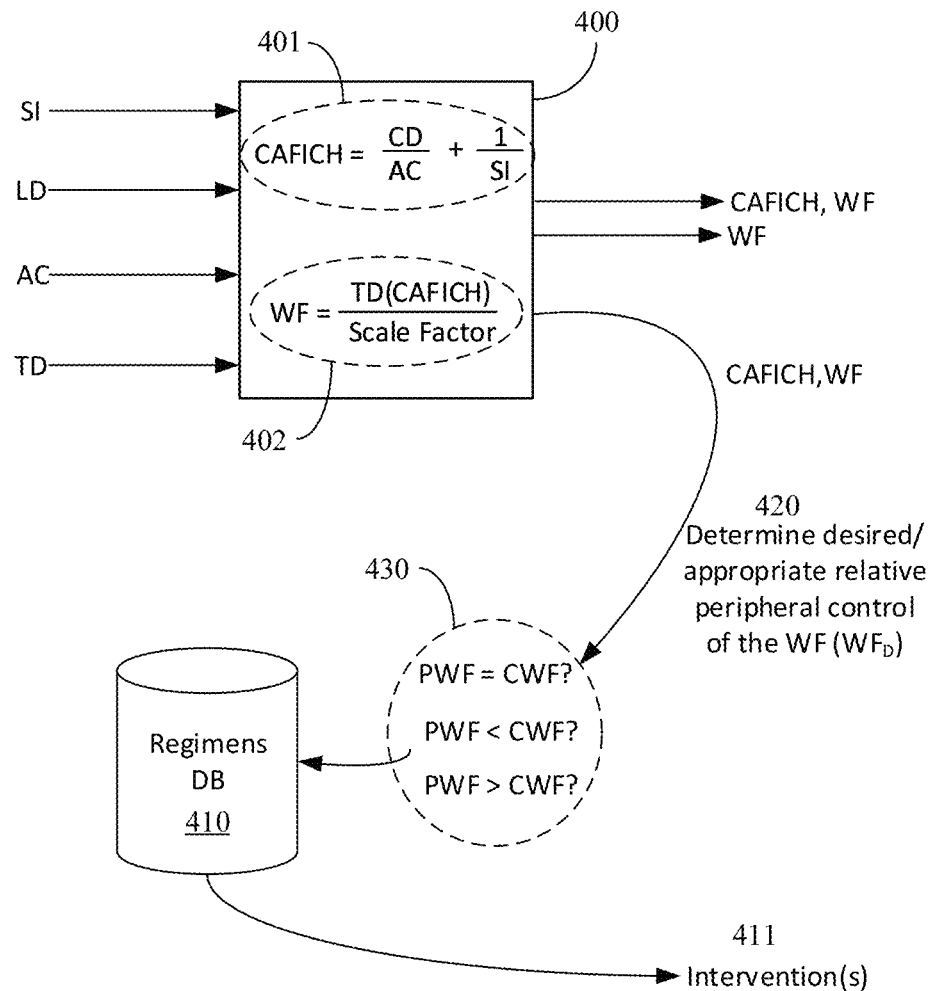
FIG. 4 illustrates cardiovascular health assessment as part of an individualized health or medicine application.

FIG. 4 illustrates cardiovascular health assessment as part of an individualized health or medicine application. As illustrated in FIG. 4, the TD, SI, LD, and AC generated according to any suitable process including those described above with respect to FIGS. 2A-2D, can be received by an evaluation system 400. At a minimum, the evaluation system 400 uses information of a subject's biometrics including heart rate, blood pressure, height, weight, and body fat percentage; and an autonomic constriction index (the AC) to generate a working tissue flow.

Evaluation system 400 may be implemented as described with respect to any of the implementations of evaluation system 110 of FIG. 1A or 1B. In addition, although TD, SI, LD, and AC are specifically described, other measures may be taken and used to enhance or modify the described algorithm.

At the evaluation system 400, the TD, SI, LD, and AC are used to generate a working tissue flow (WF), which can be provided as an output of the system 400. For example, the evaluation system can calculate WF=(TD*[(LD/AC)+1/SI])/ScaleFactor, where the ScaleFactor can be based on the individual.

The system 400 may generate the WF by determining a value indicative of a resistance in the vessel bed of the subject using the stiffness index (SI), the local dilation response (LD), and the autonomic constriction index (AC); and then determining the working tissue flow of the subject by dividing the measured total blood drive (TD) with the value indicative of the resistance in the vessel bed of the subject. In some cases, such as involving a tracker such as described with respect to FIG. 1B, in response to receiving an updated measure (e.g., from the tracker) that is associated with at least one of the TD, the SI, the LD, or the AC, the system can determine an updated value indicative of the resistance in the vessel bed of the subject; and, thus, determine an updated working tissue flow of the subject.

In one implementation, a CAFICH score is first generated (401). In a simple form, the CAFICH score=(LD/AC)+(1/SI). Of course, as mentioned above, other measures may be used to enhance or modify this algorithm. The CAFICH sore generation allows assessment of the ability to supply blood to working tissue (Working Tissue Flow or WF). The resistance in the vessel bed is proportional to the reciprocal of the CAFICH score. Since WF can be calculated as [TD/(resistance in the vessel bed)], WF can be generated (402) by WF=(TD (CAFICH))/ScaleFactor.

As mentioned above, the WF can be output by the system 400. The WF can be provided as a WF value (e.g., as a volume per unit time) as well as, or as an alternative, be provided in the form indicating a relative peripheral control of the WF (represented in the drawing as CAFICH, WF). The WF, particularly the relative peripheral control of the WF, can be provided as an output with some visual indicator to a user of the evaluation system 400 and/or provided for use in obtaining an individualized intervention, for example, by a medicine or health application incorporating the cardiovascular health assessment. The medicine or health application can enable users to indicate desired fitness or health objectives and then use those desired fitness or health objectives to identify interventions 411 from, for example, a storage resource storing a regimens database 410 (or other data structure for the regimen/intervention information).

In the illustrative example, in response to receiving an indication of a desired fitness or health objective, the system (e.g., system 400) can determine (420) a desired value or range for the relative peripheral control of working tissue flow (WFD). The system (e.g., system 400) can determine (430) the relationship between WF and WFD, use that relationship to identify at least one appropriate intervention 411, and then provide the at least one intervention 411 from the stored health and fitness regimens 410 as output. For example, the determination can include determining, from the WF, particularly the relative peripheral control of working tissue flow, whether PeripheralWF=CentralWF, PeripheralWF<CentralWF, or PeripheralWF>CentralWF; and then comparing the result to a desired outcome for regimen design.

The at least one intervention 411 can be selected to increase or decrease the relative peripheral control of the working tissue flow based on moving the relative peripheral control of the working tissue flow to the desired value or range of the relative peripheral control of working tissue flow. In some cases, improvement to overall WF may be desired in addition to adjustment to relative peripheral control of WF. In addition, interventions 411 may still be provided even where the relative peripheral control of working tissue flow is at or within the desired value or range for the relative peripheral control of working tissue flow as it can be desirable to identify regimens that maintain the relative peripheral control of the WF.

For example, in response to receiving an indication of improved cardiovascular health as the indication of the desired fitness or health objective, the system can determine the total working flow and whether the degree to which the total working tissue flow is limited at the central or peripheral level. A relative peripheral control value or range corresponding to CAFICH can be generated and compared to both the population normal and the desired fitness or health objective. If it is found that the subject is peripherally limited as compared to the desired peripheral control flow value or range, the system can provide one or more interventions to increase vessel relaxation response as the at least one regimen. When it is determined that working flow is centrally limited as compared to the desired flow value or range, the system can provide one or more regimens to decrease centrally controlled basal vessel tone as the at least one regimen.

Working tissue flow limits athletic performance and also determines the degree of functionality and likelihood of cardiovascular events in patients with cardiovascular disease. In the athlete, the working tissue in the primary demand muscle group, such as the legs of a cyclist, ice skater, runner or rower. In the cardiovascular disease patient, the direct working tissue is often the coronary artery, which cannot be directly measured but is approximated by peripheral tissue. The subject techniques include peripheral measures as it is a significant component of TD. Thus, one of the outputs of the algorithm is working tissue flow (WF).

From simple measures of LD, AC, and SI measured and calculated from Pulse Wave analysis performed at rest and after a maximal exercise test, it is possible to effectively assess the maximal alteration in blood flow that an individual can achieve in a specific vascular bed. When combined with CO measures one can assess the relative importance of peripheral and central components of the cardiovascular system. An understanding of these relative contributions is valuable in determining the appropriate approach to improving cardiovascular health. Understanding WF, and the level of relative peripheral control, to the tissue allows assessment of how well an individual can respond to stress. The stress, for a patient with significant vascular disease, may be as simple as walking. Whereas, for an athlete such as a hockey player, the stress may be as complex as ice time.

In various implementations, the algorithm can be expanded to include a dynamic response element that can be used to assess WF in different tissues and at different workloads. Using the CAFICH score allows for assessment of where that limitation lies and thus it is possible to optimize training/rehab to allow for maximal improvement in function.

Other parameters can be incorporated in the CAFICH score. For instance, there are other measures that can be used from Pulse Wave Analysis that may increase the probity of the algorithm, e.g., notch ratio that can be used as a corollary of AC.

Figure 5A:
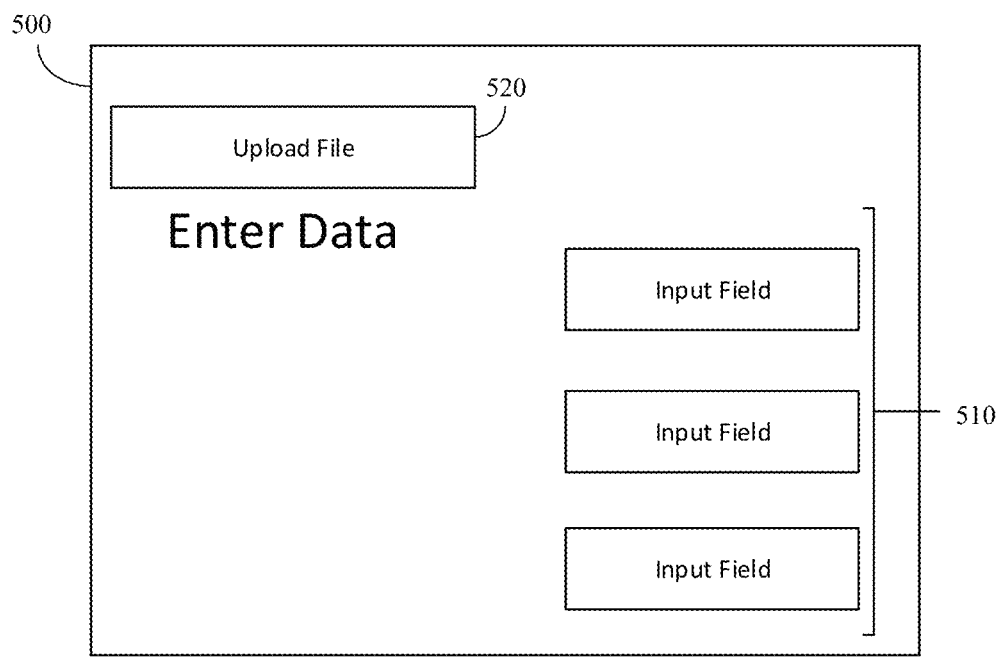
FIGS. 5A and 5B illustrate representational user interfaces for an example scenario.
Figure 5B:
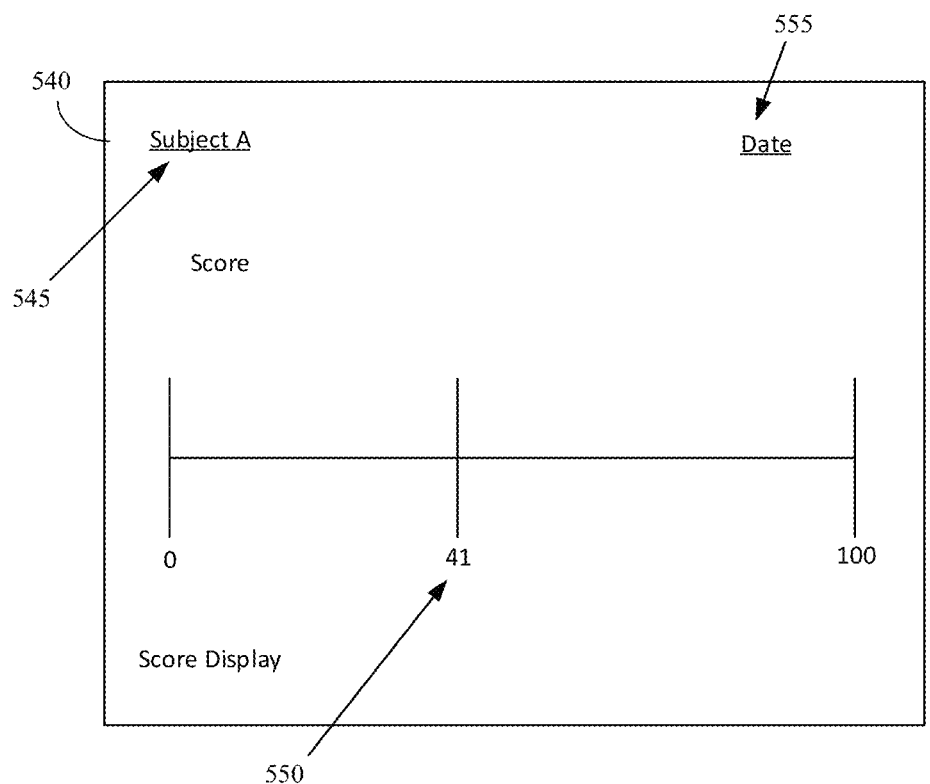

FIGS. 5A and 5B illustrate representational user interfaces for an example scenario. Referring to FIG. 5A, in a graphical user interface 500 to an evaluation system, a user can provide information via one or more input fields 510. In some cases, information about a subject may be stored in a file. The graphical user interface 500 to the evaluation system can provide functionality to enable the file to be uploaded to the evaluation system (e.g., upload file command 520). For example, results of the various tests may be entered and/or the pulse wave forms can be provided for analysis by the evaluation system. In addition, a subject's weight, height, and other information may be input either via a field or as part of a file.

After receiving the appropriate information, the evaluation system can generate a working tissue flow for the subject; and provide a value representing relative peripheral control for display to the user, as shown in FIG. 5B. Referring to FIG. 5B, a result 550 for Subject A 545 is shown in a graphical user interface 540, reflecting the relative peripheral control of working tissue flow for that subject 545 on a particular date 555. In this example, the result 550 is shown on a plot line graphically representing where in the range of 0 to 100 that the relative peripheral control of the working tissue flow lies, where 0 would represent completely centrally/cardio limited and 100 would represent completely peripherally limited). This result 550 can be provided on its own. However, its significance is best understood when taken in context of a desired objective and the total working flow. For example, in a fitness scenario, the subject may desire to improve their ability to run a marathon or the subject may desire to improve their strength in lifting weights.

Figure 6A:
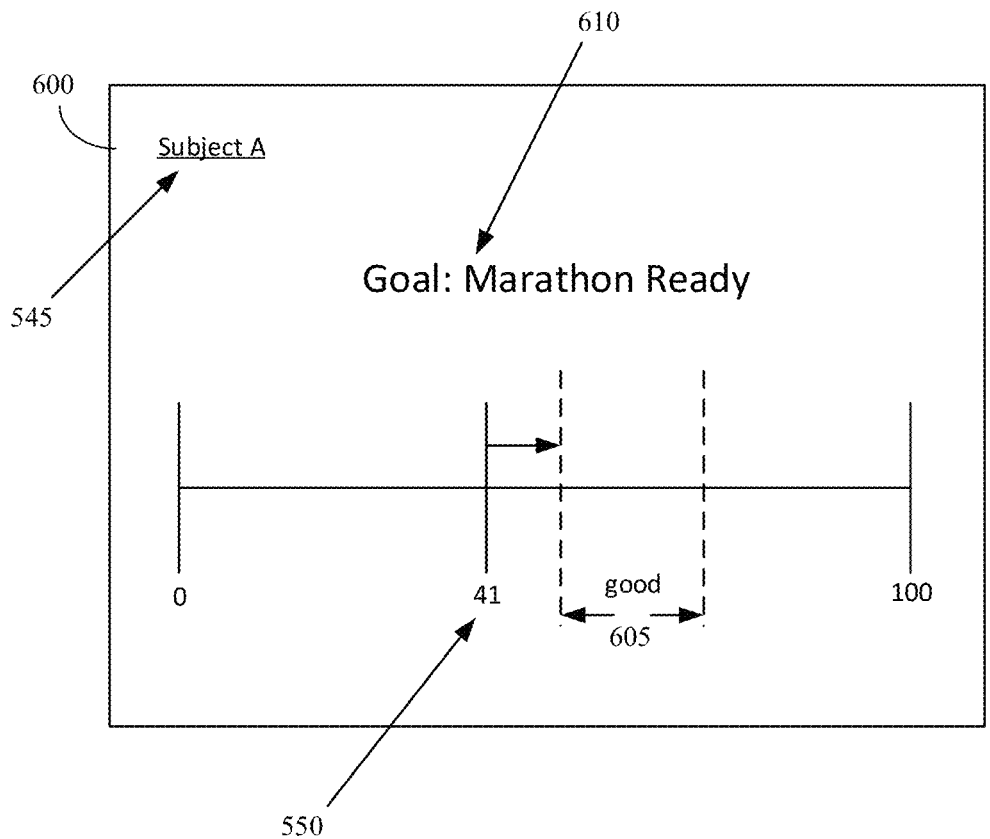
FIGS. 6A and 6B illustrate representational user interfaces for an example training scenario.
Figure 6B:
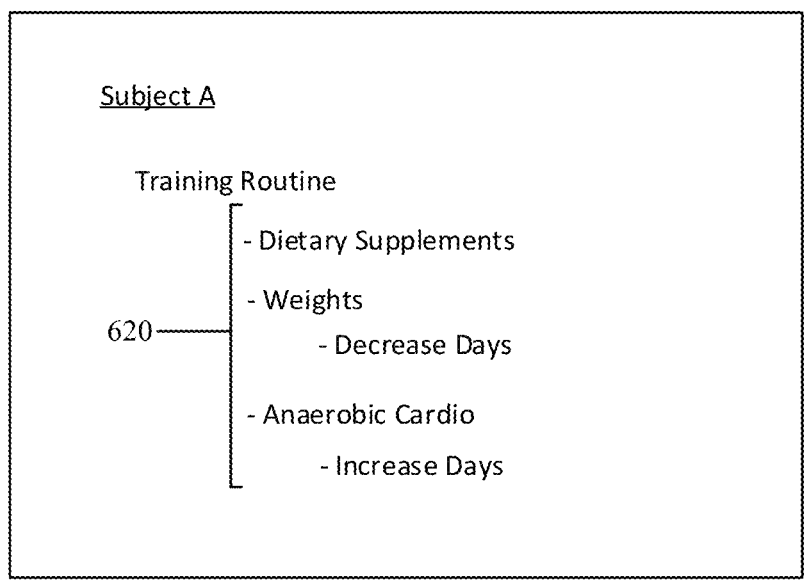

FIGS. 6A and 6B illustrate representational user interfaces for an example training scenario. Referring to FIGS. 6A and 6B, in a case where a subject desires improved performance in running a marathon, that goal may be input to the evaluation system by a user (for example, via an input field 510 such as described with respect to FIG. 5A). The evaluation system can have or access data on ranges for both working tissue flow and relative peripheral control that reflect an appropriate range for achieving the subject's goal of being marathon ready. As illustrated in FIG. 6A, the graphical user interface 600 can display the "good" range 605 for the relative peripheral control value for achieving the subject's goal 610. As can be seen, Subject A's relative peripheral control value 540 is outside of the desired range 605. As a result, the evaluation system can generate one or more individualized interventions 620 and provide them to the user as illustrated in FIG. 6B. In this example, the individualized interventions 620 for subject A 545 include dietary supplements, instructions regarding weights and instructions regarding anaerobic cardio.

Figure 7A:
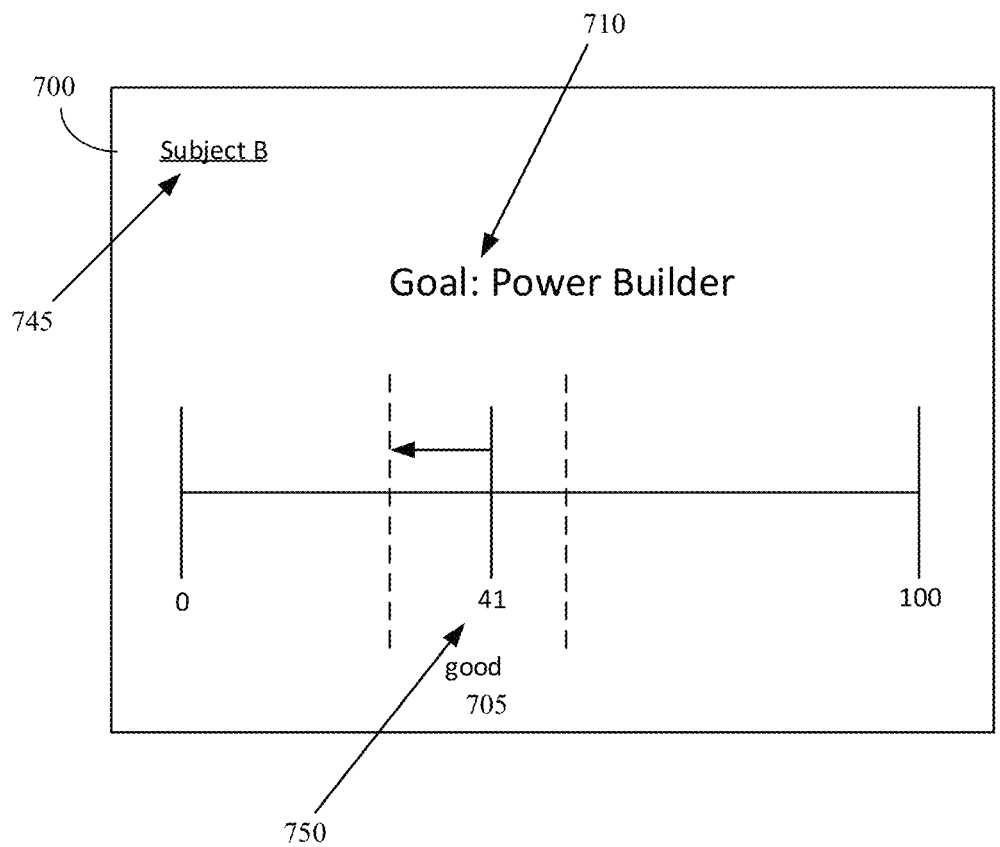
FIGS. 7A and 7B illustrate representational user interfaces for an example training scenario.
Figure 7B:
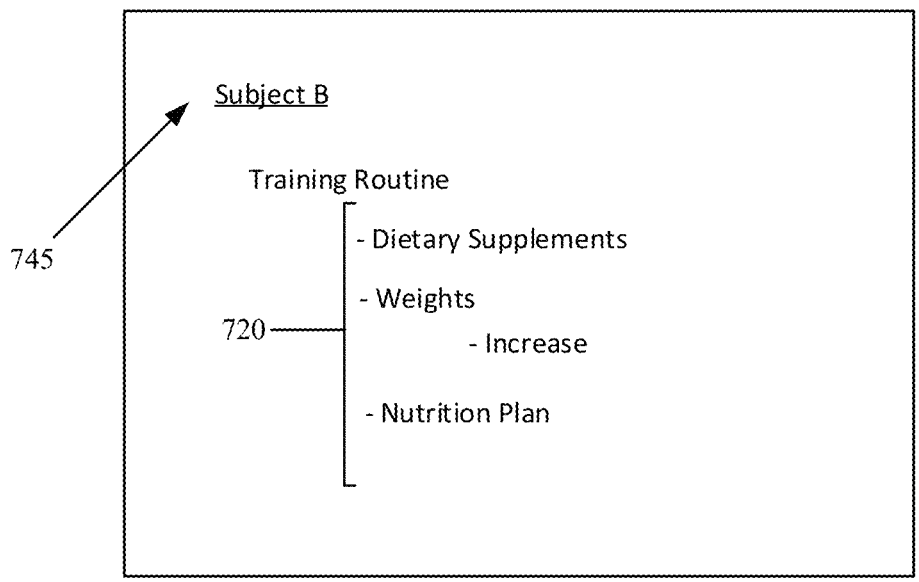

FIGS. 7A and 7B illustrate representational user interfaces for an example training scenario. Referring to FIGS. 7A and 7B, in a case where a subject desires improved performance in their power lifting capabilities, that goal may be input to the evaluation system by a user (for example, via an input field 510 such as described with respect to FIG. 5A). The evaluation system can have or access data on ranges for both working tissue flow and relative peripheral control that reflect an appropriate range for achieving the subject's goal of improving the weights they can lift. As illustrated in FIG. 7A, the graphical user interface 700 can display the "good" range 705 for the relative peripheral control for achieving the subject's goal 710. As can be seen, the relative peripheral control 750 of subject B 745 is within the desired range 705. As a result, the evaluation system can generate one or more individualized interventions 720, which may be based on incrementally improving the subject's working tissue flow and relative peripheral control within the good range 705 or just maintaining the subject's working tissue flow within the range 705. The individualized interventions 720 may be provided as illustrated in FIG. 7B. In this example, the individualized interventions 720 for subject B 745 include dietary supplements, instructions regarding weights, and instructions regarding a nutrition plan.

As can be seen when comparing FIGS. 6A and 6B with 7A and 7B, a similar set of working tissue flow of a subject may have a different individualized intervention depending on the subject's goals and the relative degree of peripheral control exhibited (due to the ideal working tissue flows for achieving those goals).

In addition to illustrating a subject's current working tissue flow with respect to a suggested "good" range, the evaluation system can be used to track a subject's working tissue flow over time, as well as automatically adjusting suggested interventions based on the direction that the subject's working tissue flow is heading (with respect to a stated goal). Furthermore, certain features of the evaluation may be carried out in real-time and over time (e.g., where measurements are taken at certain intervals to reevaluate and/or adjust suggested interventions).

In some cases, a baseline cardiovascular health assessment may be obtained and then, through the use of wearable or otherwise mobile devices, one or more of the individual input variables can be assessed and a relative performance value calculated that can be related in real-time to workload.

In some cases, aspects of the described evaluation system can be integrated with fitness trackers (e.g., available on a mobile phone and/or wearable such as a FITBIT from Fitbit, Inc., or Samsung smartwatch or Apple Watch).

In addition to health and fitness scenarios illustrated herein, the described evaluation system can be suitable for military and/or security and/or emergency personnel. For example, the evaluation system can be used to carry out an assessment for personnel to identify interventions to support those individuals needing to operate at peak performance. The evaluation system can be used to predict the individuals that may perform the best for certain scenarios as well as provide real time assessments. Physiological measurements can be obtained via sensors or modifications to equipment or clothing that can capture on an ongoing basis the information needed by the system to generate real time assessments.

FIG. 8 shows a block diagram illustrating components of a computing device that may implement or communicate with an evaluation system. Computing device 800 can represent any personal computer or computing component with user interface. For example, computing device 800 can be, but is not limited to, a desktop, a notebook or laptop computer, a tablet, a smart phone, a wearable computing device (e.g., watch, glasses, textile) or a computing component of a medical instrument.

Computing device 800 includes at least one hardware processor 805 that processes data according to instructions of an operating system 808 and one or more application programs 810 stored on a storage system 815. The one or more application programs 810 can include certain aspects carried out by an evaluation system and/or medicine or health application and/or software that communicates with an evaluation system and renders user interfaces such as illustrated in FIGS. 5A, 5B, 6A, 6B, 7A, and 7B. In some cases, application programs 810 may include programs used for certain medical instruments.

Storage system 815 can include any computer readable storage media readable by the at least one hardware processor 805 and capable of storing software including the operating system 808 and the one or more application programs 810. Storage system 815 may include volatile and nonvolatile, removable and non-removable media implemented in any method or technology for storage of information. Examples of storage media include random access memory, read only memory, magnetic disks, optical disks, CDs, DVDs, flash memory, magnetic cassettes, magnetic tape, magnetic disk storage or other magnetic storage devices, or any other suitable non-transitory storage media.

The computing device 800 can further include user interface system 830, which may include input/output (I/O) devices and components that enable communication between a user and the system 800. User interface system 830 can include input devices such as a mouse, track pad, keyboard, a microphone, and other types of input devices and their associated processing elements capable of receiving user input. The user interface system 830 may also include output devices such as display, speakers, haptic devices, and other types of output devices.

Visual output may be depicted on the display in myriad ways, presenting graphical user interface elements, text, images, video, notifications, virtual buttons, virtual keyboards, or any other type of information capable of being depicted in visual form.

Computing device 800 may also include a communications interface 835 that may include communications connections and devices that allow for communication with other computing systems over one or more communication networks (not shown). Examples of connections and devices that together allow for inter-system communication may include network interface cards, antennas, power amplifiers, RF circuitry, transceivers, and other communication circuitry. The connections and devices may communicate over communication media (such as metal, glass, air, or any other suitable communication media) to exchange communications with other computing systems or networks of systems.

It should be understood that any computing device implementing computing device 800 may have more or fewer features or functionality and is not limited to the configurations described herein.

FIG. 9 illustrates a block diagram of a computing system that may implement the evaluation system as a service platform. Referring to FIG. 9, system 900 may be implemented within a single computing device or distributed across multiple computing devices or sub-systems that cooperate in executing program instructions. The system 900 can include one or more blade server devices, standalone server devices, personal computers, routers, hubs, switches, bridges, firewall devices, intrusion detection devices, mainframe computers, network-attached storage devices, and other types of computing devices. The system hardware can be configured according to any suitable computer architectures such as a Symmetric Multi-Processing (SMP) architecture or a Non-Uniform Memory Access (NUMA) architecture.

The system 900 can include a processing system 905, which may include one or more hardware processors and/or other circuitry that retrieves and executes software 910, including software for carrying out evaluation system processes 915, from storage system 920. Processing system 905 may be implemented within a single processing device but may also be distributed across multiple processing devices or sub-systems that cooperate in executing program instructions.

Examples of processing system 905 include general purpose central processing units, graphic processing units, application specific processors, and logic devices, as well as any other type of processing device, combinations, or variations thereof. The one or more processing devices may include multiprocessors or multi-core processors and may operate according to one or more suitable instruction sets including, but not limited to, a Reduced Instruction Set Computing (RISC) instruction set, a Complex Instruction Set Computing (CISC) instruction set, or a combination thereof. In certain embodiments, one or more digital signal processors (DSPs) may be included as part of the computer hardware of the system in place of or in addition to a general-purpose CPU.

Storage system(s) 920 can include any computer readable storage media readable by processing system 905 and capable of storing software 910. Storage system 920 may include volatile and nonvolatile, removable and non-removable media implemented in any method or technology for storage of information. Examples of storage media include random access memory, read only memory, magnetic disks, optical disks, CDs, DVDs, flash memory, magnetic cassettes, magnetic tape, magnetic disk storage or other magnetic storage devices, or any other suitable storage media. In some cases, storage system 920 can include virtual memory hosted on a hardware system. In no case is the storage medium of storage system 920 a transitory propagated signal or carrier wave.

Storage system 920 may be implemented as a single storage device but may also be implemented across multiple storage devices or sub-systems co-located or distributed relative to each other. Storage system 920 may include additional elements, such as a controller, capable of communicating with processing system 905.

System 900 can include communication interface 925, providing communication connections and devices that allow for communication between system 900 and other computing systems over a communication network or collection of networks or the air.

System 900 can also include or communicate with a storage resource 930 that stores intervention regimens.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

Embodiments may be implemented as a computer process, a computing system, or as an article of manufacture, such as a computer program product or computer-readable storage medium. Certain methods and processes described herein can be embodied as software, code and/or data, which may be stored on one or more storage media. Certain embodiments of the invention contemplate the use of a machine in the form of a computer system within which a set of instructions, when executed, can cause the system to perform any one or more of the methodologies discussed above. Certain computer program products may be one or more computer-readable storage media readable by a computer system and encoding a computer program of instructions for executing a computer process.

By way of example, and not limitation (other than the explicit disclaimer below), computer-readable storage media may include volatile and non-volatile memories, removable and non-removable media implemented in any method or technology for storage of information such as computer-readable instructions, data structures, program modules or other data. Examples of computer-readable storage media include volatile memory such as random access memories (RAM, DRAM, SRAM); non-volatile memory such as flash memory, various read-only-memories (ROM, PROM, EPROM, EEPROM), phase change memory, magnetic and ferromagnetic/ferroelectric memories (MRAM, FeRAM), and magnetic and optical storage devices (hard drives, magnetic tape, CDs, DVDs). As used herein, in no case does the term "storage media" consist of transitory carrier waves or propagating signals.

A greater understanding of the present invention and of its many advantages may be had from the following examples and case studies. The following examples are illustrative of the effectiveness of the described techniques to identify neurodevelopmental issues. They are, of course, not to be considered in any way limitative of the invention. Numerous changes and modifications can be made with respect to the invention.

Example: Evaluation of Two Young Males

Figure 10:
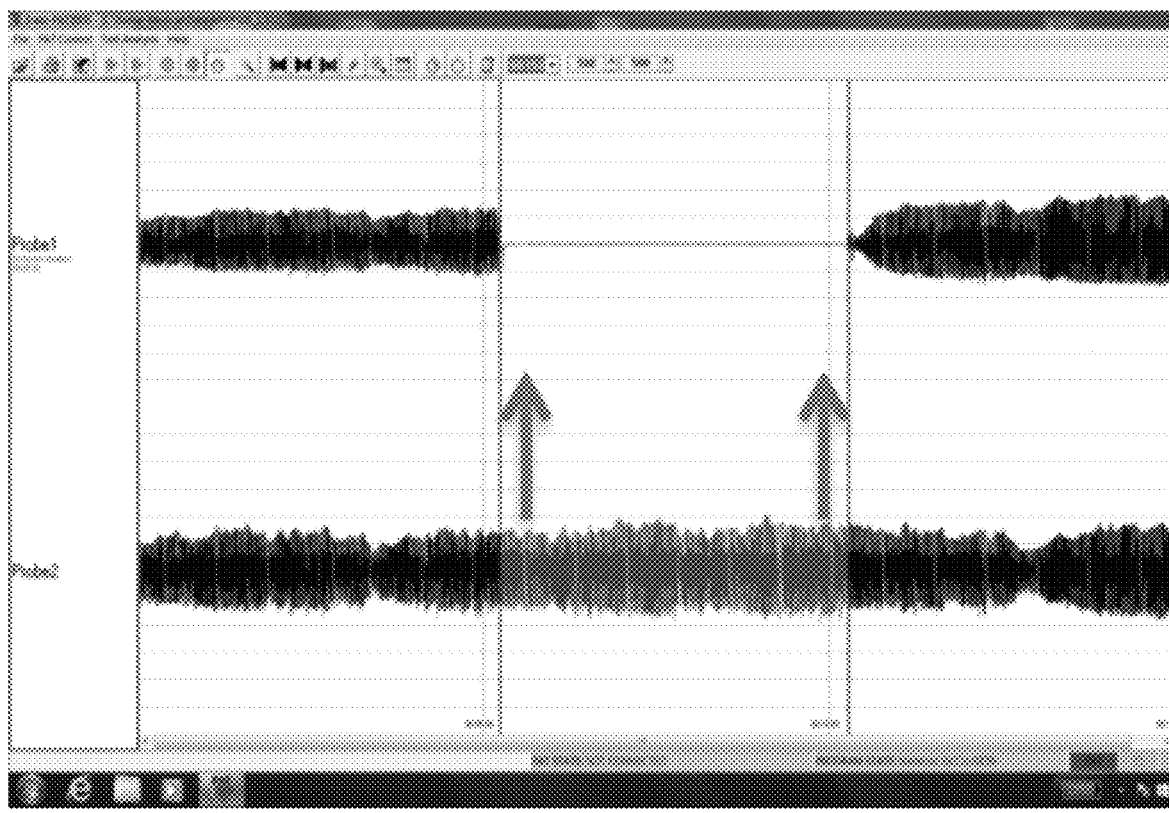
FIG. 10 shows a pulse plethysmography measurement for subject 1 in the illustrative evaluation of two subjects.

Subject 1—"Peripheral Dominant": Nick is 23 years old with a resting heart rate of 60 and Blood Pressure of 98/56. He is 5'4" tall and 121 lbs giving him a BMI of 20.66. FIG. 10 shows a pulse plethysmography measurement for Nick in response to vessel occlusion (initiated and stopped at arrows). His average resting Pulse Wave Amplitude (PWA) is 378 with a maximal increase in dilation of 1.509 under hyperemic stress. However, his control response is 1.295, meaning that his RHI is only 1.48 (<1.6). From Nick's RHI score one would consider him a person with poor endothelial function.

Figure 11:
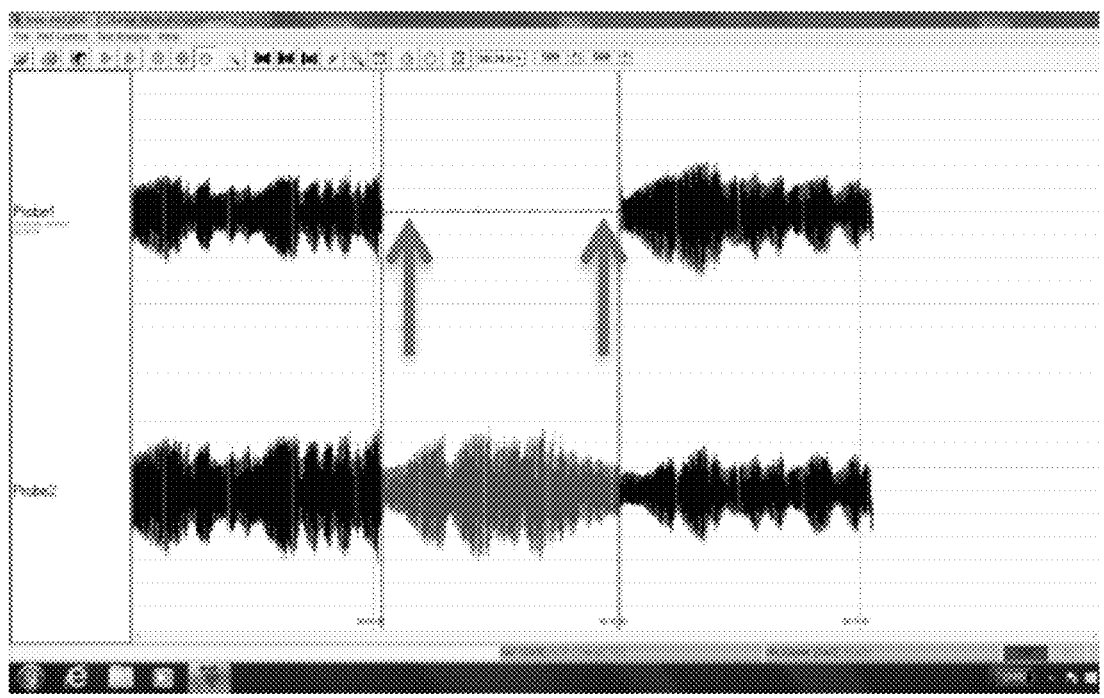
FIG. 11 shows a pulse plethysmography measurement for subject 2 in the illustrative evaluation of two subjects.

Subject 2—"Central Dominant": Robert is 24 years old with a resting heart rate of 57 and BP of 141/66. He is 6' tall and 190 lbs giving him a BMI of 25.74. FIG. 11 shows a pulse plethysmography measurement for Robert in response to vessel occlusion (initiated and stopped at arrows). His average resting Pulse Wave Amplitude (PWA) is 525 with a maximal increase in dilation of 1.673 under hyperemic stress. However, his control response is 0.856, meaning that his RHI is 2.36 (>1.6). From Robert's RHI score one would classify him as a person with good endothelial function.

TABLE 1

| Factor | Nick | Robert |
| --- | --- | --- |
| At Rest | | |
| Total Blood Flow (Q) | 4 L/min | 5.26 L/min |
| Pressure differential (ΔP) | 42 | 75 |
| Relative resistance (Q/ΔP) | 0.095 | 0.07 |
| PWA | 378 | 525 |
| Relative Flow (Rx PWA) | 35.9 | 36.8 |

TABLE 1-continued

| Factor | Nick | Robert |
| --- | --- | --- |
| At Maximal Exercise | | |
| Total Blood Flow (Q) | 5.7 | 7.5 |
| Pressure differential (ΔP) | 80 | 120 |
| Relative resistance (Q/ΔP) | 0.071 | 0.0625 |
| PWA | 567 | 840 |
| Relative Flow (Rx PWA) | 40.25 | 52.5 |

Nick is leaner than Robert and has a lower cardiovascular demand at rest than Robert. However, when given a hyperemia test he appears to have a poor vascular response, as his RHI is only 1.48 when measured in the non-dominant arm. Robert on the other hand has a strong vascular response, as his RHI is 2.36. However, closer examination of the response of their other arm (used as internal control) indicates how autonomic constriction is contributing to the response. The local dilation response in both Nick and Robert is close to 1.5, but Nick also has an increase in vasodilation in the control arm, while Robert has a constriction. It is this difference that defines them as Peripheral and Central dominant, as central autonomic mechanisms are driving the vasoconstriction in Robert's control arm. These differences are further exaggerated with maximal exercise, where Nick's higher level of vascular tone leads to a relative increase in CO (57% vs 40% for Robert), but a lower differential change in relative flow (4.3 vs 15.7 for Robert). Thus, Nick is maximized in CO during exercise, but has limited vessel responsiveness. Using CAFICH Nick would be found to have a poor relative peripheral control value.

This example demonstrates that to improve cardiovascular health, Nick would need to increase his vessel relaxation response (through appropriate exercise and diet). The opposite is true for Robert, where his limitation is in CO, which requires an entirely different training/diet regime to produce improvement. Both of these individuals are young and relatively healthy, but without this concerted approach one would not be able to understand where their limits to cardiovascular fitness lay. While this may not present an issue in the general population, it will be of significant importance for both athletes and individuals with impaired cardiovascular health.

Example: Endothelial Function Study

Figure 12A:
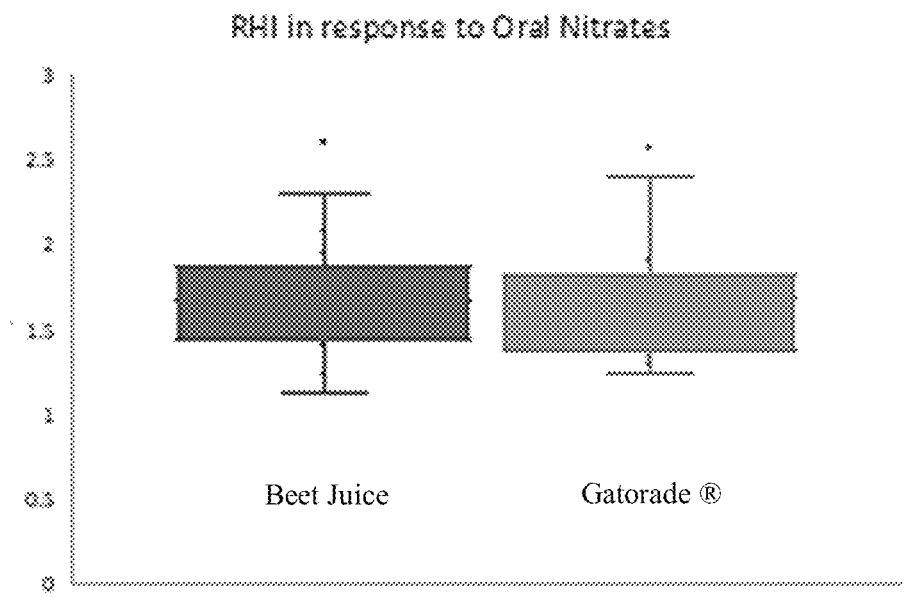
FIG. 12A shows a box and whisker plot of the endothelial function study using peripheral arterial tone signal.

Endothelial function measurements (for determining Reactive Hyperemic Index (RHI)) using a peripheral arterial tone signal may be challenging in subjects with responsive vasculature. A study was conducted on the role of a particular polymorphism on endothelial function. Twenty-two college age students were recruited and their response to Beet juice (a source of nitrates) was examined. Using RHI generated using peripheral arterial tone signal as the baseline parameter, the average value was 1.68±0.355 with 10 of the 22 subjects scoring less than the 1.6 which is used to determine cardiovascular health. Furthermore there was little shift when the subjects were given a known vasodilator agent (Oral nitrates in the form of beet juice). The average RHI post beets was 1.71±0.391. FIG. 12A shows a box and whisker plot of the endothelial function study using peripheral arterial tone signal. Referring to FIG. 12A, the box and whisker plot demonstrates a lack of responsiveness and the poor prognostic value of RHI generated using peripheral arterial tone signal. Using the raw data from these experiments, the hyperemic response was recalculated using the LD measure derived from the maximal change in pulse amplitude post hyperemia (see e.g., method described with respect to FIG. 2C).

Figure 12B:
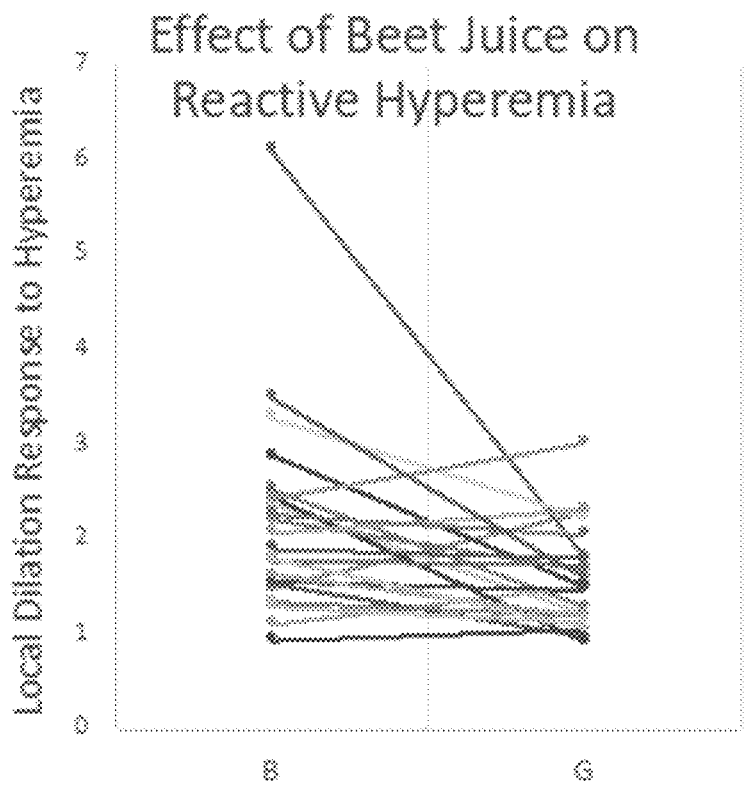
FIG. 12B shows a plot of a local dilation response to hyperemia generated according to an embodiment described herein.

FIG. 12B shows a plot of a local dilation response to hyperemia generated according to an embodiment described herein. The response to oral nitrates was studied to provide a measure of effectiveness of using the LD measure. In this study, the average LD was 2.17 in the presence of beets, and only 1.56 in the control (Gatorade®), furthermore 17 of the 22 subjects saw an improvement in vascular response. These data support the use of LD as a measure of endothelial function in the young.

Example: Stiffness Index Using Sphygmomanometer

Figure 13A:
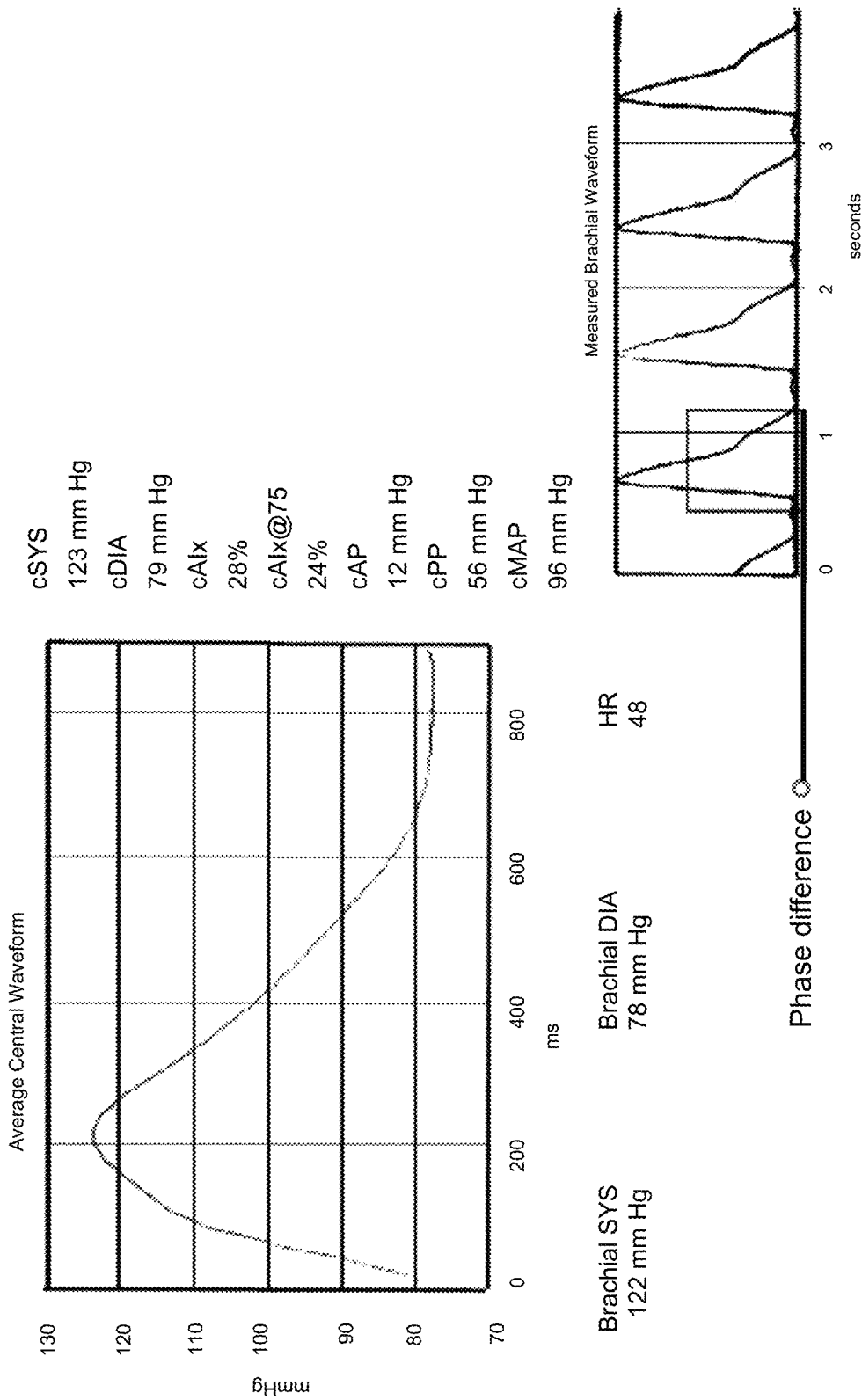
FIGS. 13A-13C show the brachial and central pulse pressure waves taken during the described study of two subjects.
Figure 13B:
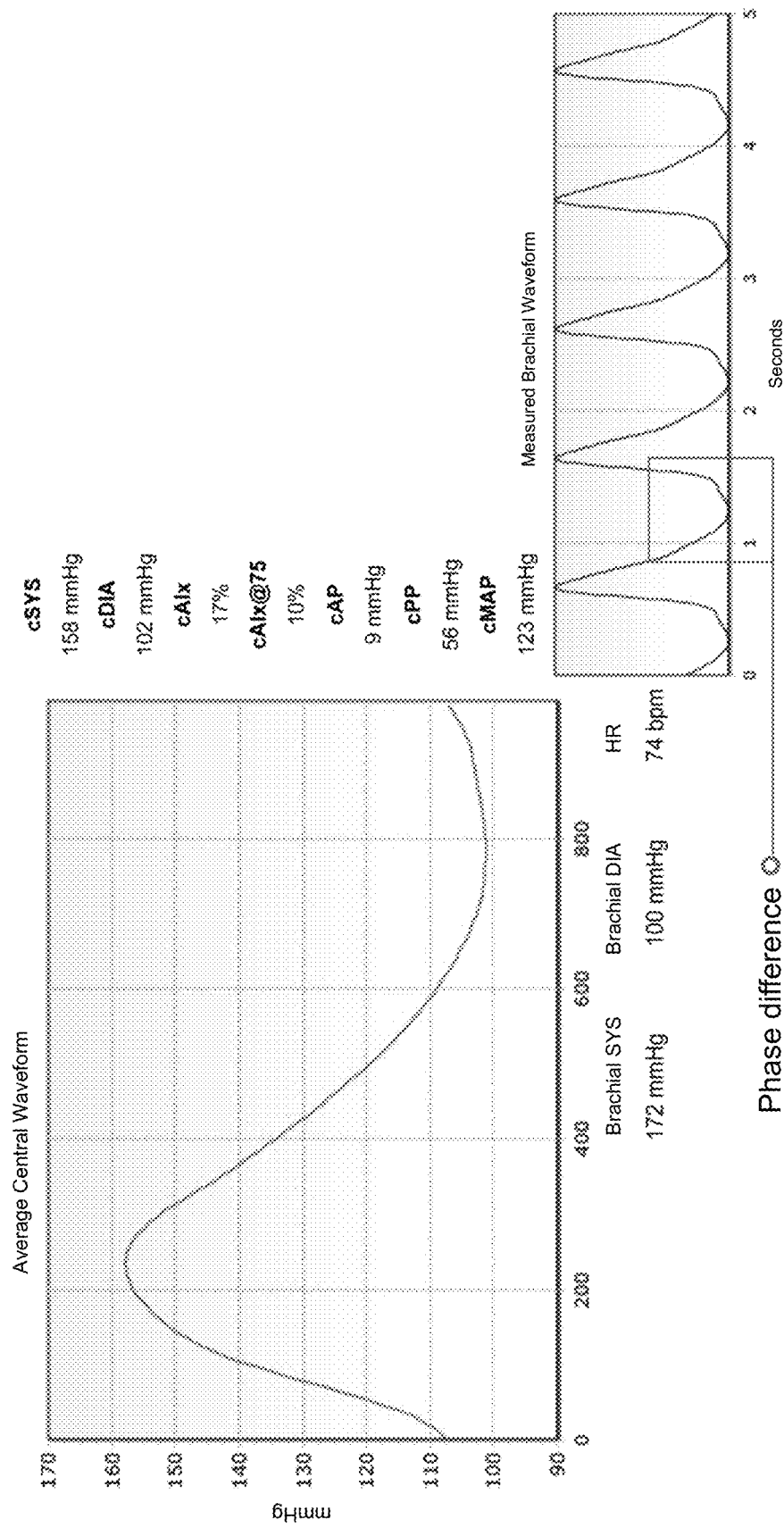
Figure 13C:
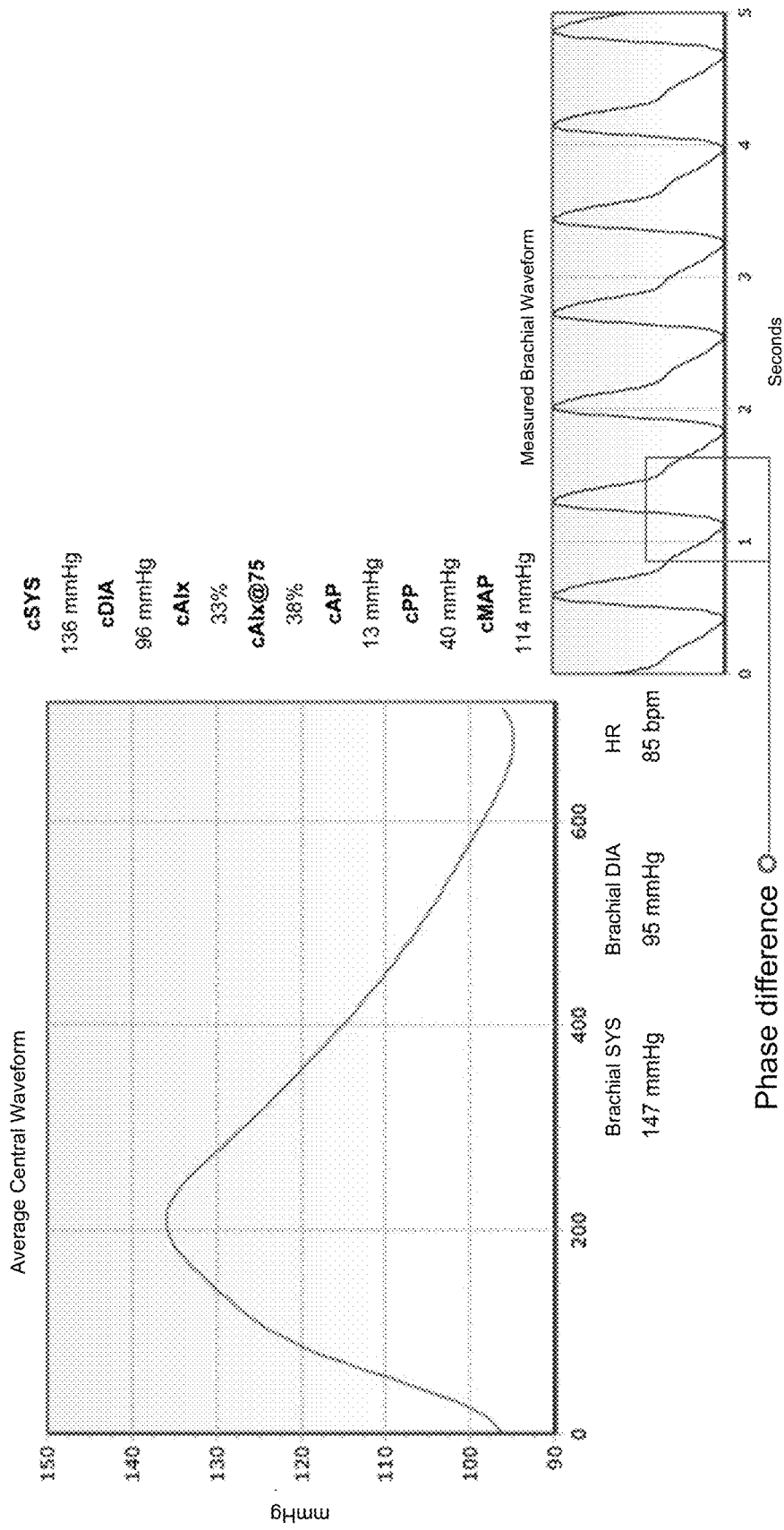

As described above with respect to processes for performing a cardiovascular health assessment, pulse wave analysis can used to estimate vascular stiffness (the stiffness index) and as a component of the scaling factor (e.g., for working tissue flow). To illustrate effectiveness of such a measure, the Oscar 2™ sphygmomanometer from SunTech Medical, Inc. was used to measure both brachial and central pulse pressure waves in two subjects. FIGS. 13A-13C show the brachial and central pulse pressure waves taken during the described study. Referring to FIG. 13A, a brachial waveform and central pulse pressure wave is shown for a healthy subject. In the healthy subject certain features are easily observed. In the brachial waveform one can observe the notch that is used to calculate the stiffness index. Also one can see that there is a sharp rise in pressure at the initiation of the systolic wave. These features are reflected in the central pressure wave where peak systole is seen at ~200 ms and there is a clear entry to diastole where the wave flattens.

A subject with hypertension, age matched to the healthy subject, is shown in FIGS. 13B and 13C, prior to and post an intervention using beets as a therapeutic. Referring to FIG. 13B, the reflective notch is barely visible due to the pronounced stiffness of the vessels. There is a delayed entry into systole in the brachial wave without a clear entry to diastole. In the central wave these characteristics are reflected in a delayed systolic peak ~270 ms and an overshoot into diastole where the waveform fails to flatten. Interestingly, as shown in FIG. 13C, when this subject ingests the vasodilator of beet juice there is a measurable improvement in waveform. The initiation of systole is restored in the brachial form and the notch is once again clearly visible. There is also a restoration of the central wave peak to ~200 ms, as well as an overall reduction in blood pressure. There is still some overshoot in the central waveform to diastole showing that not all reactivity is restored. These data demonstrate the sensitivity of including pulse wave analysis in the calculation of the CAFICH score.

Example: Autonomic Constriction and Local Dilation

Figure 14A:
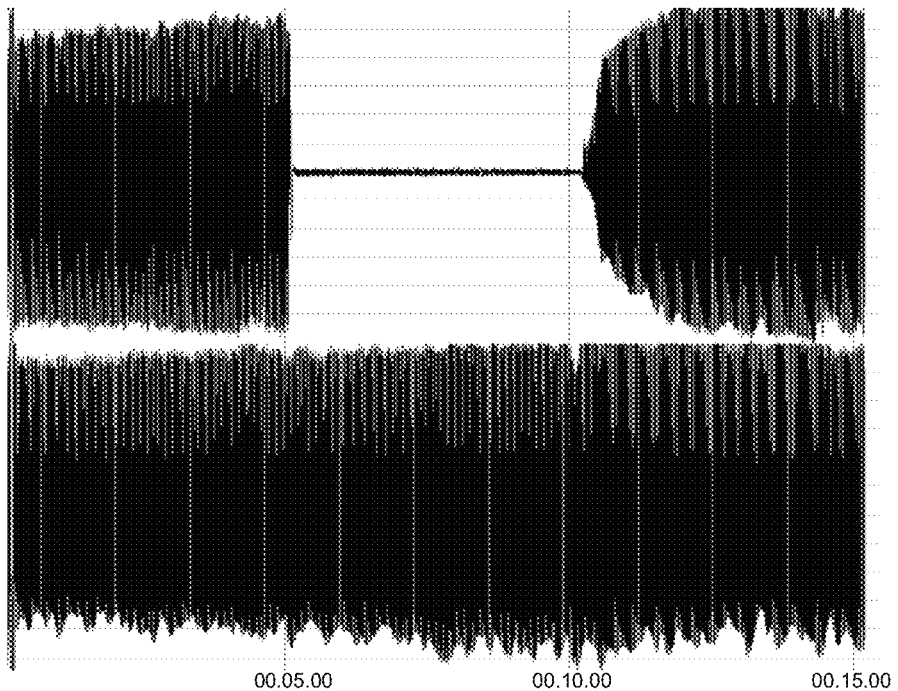
FIGS. 14A-14D show a comparison of a pressure output (peripheral arterial tone signal) in the described study of two subjects.
Figure 14B:
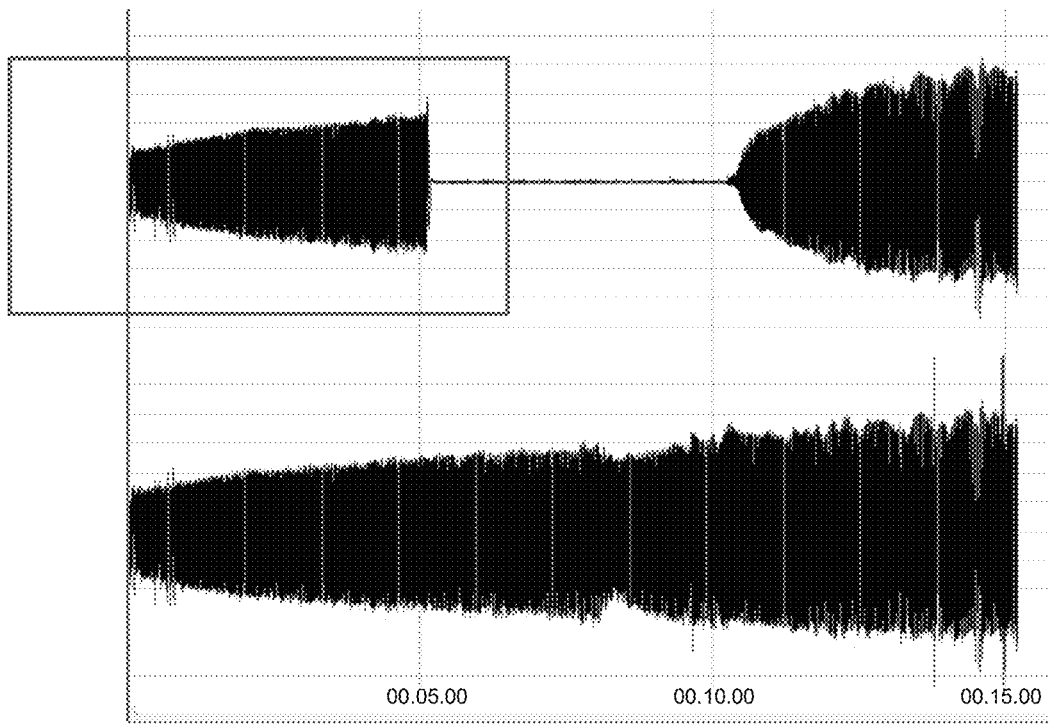
Figure 14C:
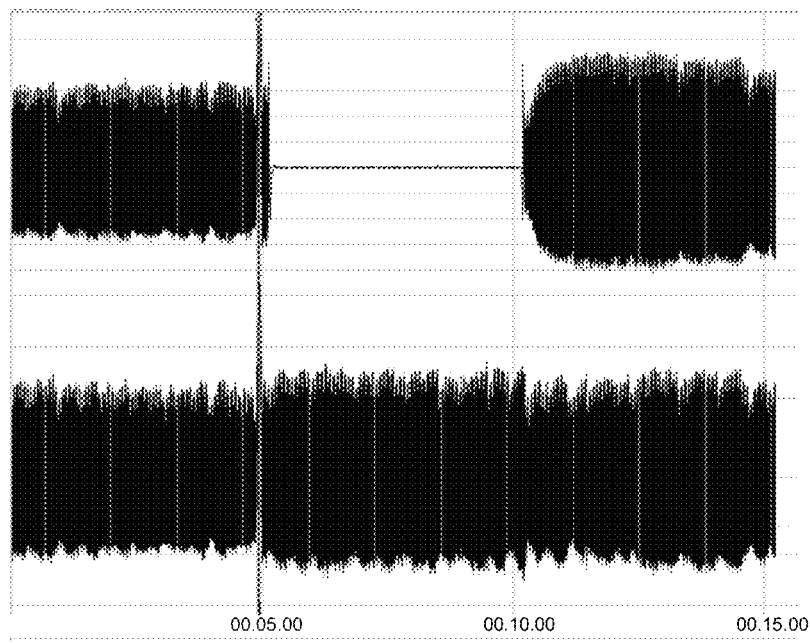
Figure 14D:
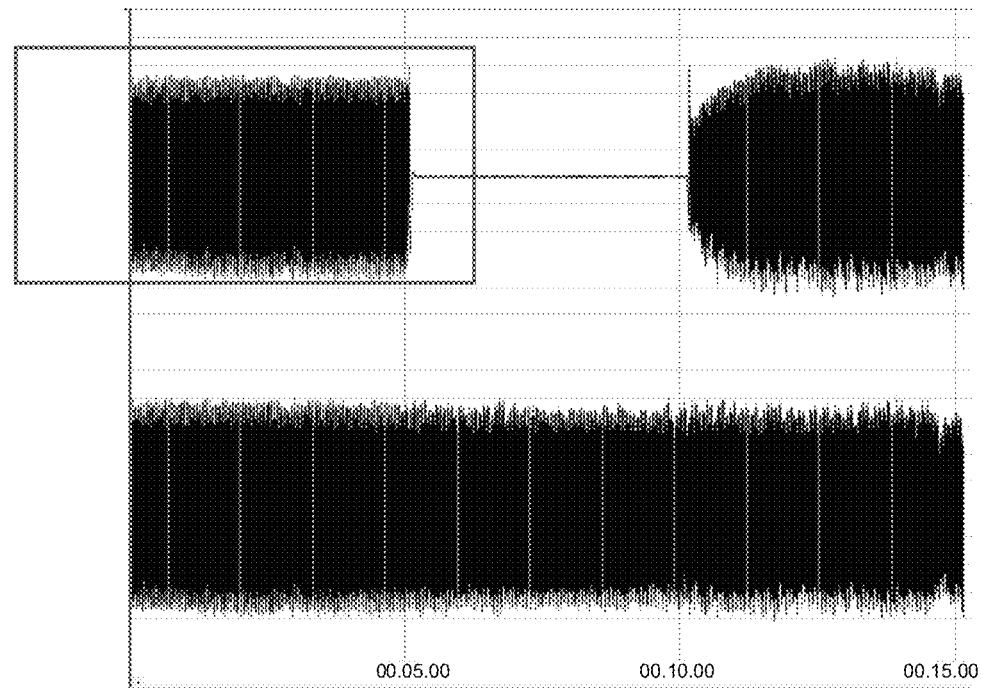

The measurement of LD was assessed with an application of an autonomic constriction (AC) stimulus. The EndoPAT™ diagnostic device from Itamar Medical Ltd. was used to compare two subjects. One subject has hypertension, and has little autonomic control as the vasculature is already maximally activated; and the other subject is normotensive (providing a control). FIGS. 14A-14D show a comparison of a pressure output (peripheral arterial tone signal) in the described study of two subjects. FIGS. 14A and 14B show the normotensive subject pre- and post activity, respectively; and FIGS. 14C and 14D show the subject with hypertension pre- and post activity, respectively. The Figures show the pressure output from the EndoPAT™ diagnostic device, indicating pulsatile volume, and, hence, vasodilation or constriction. FIGS. 14A and 14C were taken with the subject at rest and FIGS. 14B and 14D were taken immediately after a maximal exercise stress test on the bike.

Interestingly, with respect to RHI using peripheral arterial tone signal, the normotensive subject has poor function (1.48) while the hypertensive has good function (1.68), however, the lack of an LD response in FIGS. 14C and 14D is clear while the control subject has a good LD response. Most dramatically, the control subject has their pulse volume reduced by 50% in response to exercise showing a strong AC response. While the hypertensive has no change in baseline pulse volume indicating a lack of an AC response. These data show that the combination of LD and AC can be used to assess vascular control and responsiveness.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims. Further, it should be understood that the examples and embodiments described herein are for illustrative purposes only and that various modifications or changes in light thereof will be suggested to persons skilled in the art and are to be included within the purview of this application.

What is claimed is:

1. An evaluation system for individualized health and fitness interventions, the system comprising:
   one or more hardware processors;
   one or more storage media; and
   an application stored on at least one of the one or more storage media that, when executed by the one or more hardware processors, direct the one or more hardware processors to at least:
      cause to display a graphical user interface to the evaluation system, the graphical user interface comprising functionality for receiving test results and subject information and generating graphical representations of a relative peripheral control of a working tissue flow, wherein the relative peripheral control indicates dependence of the working tissue flow on central and peripheral factors on a spectrum from cardiac limited to vascular limited;
      receive, via the graphical user interface, an indication to generate a working tissue flow of a subject;
      in response to the indication to generate the working tissue flow of the subject, determine the working tissue flow of the subject and generate a graphical representation of the relative peripheral control of the working tissue flow of the subject, wherein the working tissue flow indicates an ability to supply blood to working tissue of the subject and is a value generated based on a measured total blood drive and a value indicative of a resistance in a vessel bed of the subject, wherein determining the working tissue flow of the subject comprises:
         receiving the measured total blood drive that represents a force on blood to pass through the vessel bed of the subject;
         receiving a stiffness index (SI) representing stiffness of arterial structure of the subject;
         receiving a local dilation response (LD) representing a hypoxic drive for dilation of a tissue of the subject;

receiving an autonomic constriction index (AC) representing constriction of the vessel bed of the subject;

calculating the value indicative of the resistance in the vessel bed of the subject using the stiffness index (SI), the local dilation response (LD), and the autonomic constriction index (AI);

identifying the relative peripheral control of the working tissue flow, wherein the relative peripheral control of the working tissue flow is proportional to the reciprocal of the value indicative of the resistance in the vessel bed; and dividing the measured total blood drive with the value indicative of the resistance in the vessel bed of the subject to determine the working tissue flow of the subject;

provide the working tissue flow and the relative peripheral control of the working tissue flow as a visual indicator in the graphical representation;

receive, via the graphical user interface, an indication of a desired fitness or health objective;

identify a corresponding value or range for a relative peripheral control of working tissue flow for the desired fitness or health objective;

cause to display, in the graphical representation, the visual indicator of the working tissue flow and the relative peripheral control of the working tissue flow in relation to the corresponding value or range for the relative peripheral control of working tissue flow for the desired fitness or health objective;

receive an update to the working tissue flow and the relative peripheral control; and cause to display, in the graphical user interface, an adjusted position of the visual indicator of the working tissue flow and the relative peripheral control in relation to the corresponding value or range for the relative peripheral control of working tissue flow for the desired fitness or health objective based on the update.

2. The system of claim 1, wherein the user interface to the evaluation system comprises a plot line graphically representing where in a range from completely centrally/cardio limited to completely peripherally limited that the relative peripheral control of the working tissue flow, as represented by the visual indicator, lies.

3. The system of claim 1, wherein the application directs the one or more hardware processors to determine the value indicative of the resistance in the vessel bed of the subject using the stiffness index (SI), the local dilation response (LD), and the autonomic constriction index (AC) by directing the one or more hardware processors to:

calculate a CAFICH score using CAFICH score=[(LD/AC)+(1/SI)] with optional scaling factors, wherein the resistance in the vessel bed is proportional to the reciprocal of the CAFICH score, wherein the CAFICH score is used to identify the relative peripheral control.

4. The system of claim 1, wherein the application further directs the one or more hardware processors to:

in response to receiving an updated measure associated with at least one of the measured total blood drive, the stiffness index, the local dilation response, or the autonomic constriction index representing constriction of the vessel bed of the subject, determine an updated value indicative of the resistance in the vessel bed of the subject and an updated relative peripheral control of the working tissue flow; and determine an updated working tissue flow of the subject.

5. The system of claim 4, wherein the application further directs the one or more hardware processors to:

provide the updated working tissue flow and the updated relative peripheral control of the working tissue flow as an updated visual indicator in the user interface to the evaluation system.

6. The system of claim 1, wherein the application further directs the one or more hardware processors to:

generate suggested interventions based on a relative position between the working tissue flow and the relative peripheral control of the subject and the corresponding value or range for the relative peripheral control of working tissue flow for the desired fitness or health objective.

7. The system of claim 1, wherein the application further directs the one or more hardware processors to:

automatically adjust suggested interventions based on the direction that the subject's working tissue flow is heading with respect to the value or range for the relative peripheral control of working tissue flow for the desired fitness or health objective.

8. The system of claim 1, wherein the visual indicator of the working tissue flow and the relative peripheral control is within the corresponding value or range for the relative peripheral control of working tissue flow for a first desired fitness or health objective while being outside of the corresponding value or range for the relative peripheral control of working tissue flow for a second desired fitness or health objective.

9. A method for generating individualized health and fitness interventions, the method comprising:

causing to display a graphical user interface to an evaluation system, the graphical user interface comprising functionality for receiving test results and subject information and generating graphical representations of a relative peripheral control of a working tissue flow, wherein the relative peripheral control indicates dependence of the working tissue flow on central and peripheral factors on a spectrum from cardiac limited to vascular limited;

receiving, via the graphical user interface, an indication to generate a working tissue flow of a subject;

receiving, via the graphical user interface an indication of a desired fitness or health objective;

in response to the indication to generate the working tissue flow of the subject, determining the working tissue flow of the subject and generating a graphical representation of the relative peripheral control of the working tissue flow of the subject, wherein the working tissue flow indicates an ability to supply blood to working tissue of the subject and is a value generated based on a measured total blood drive and a value indicative of a resistance in a vessel bed of the subject;

identifying the relative peripheral control of the working tissue flow, wherein the relative peripheral control of the working tissue flow is proportional to the reciprocal of the value indicative of a resistance in the vessel bed;

identifying a corresponding value or range for a relative peripheral control of working tissue flow for the desired fitness or health objective;

determining an extent to which the relative peripheral control of the working tissue flow shows that the subject is peripherally limited or centrally limited with respect to a value or range of a corresponding relative peripheral control of working tissue flow for the desired fitness or health objective;

causing to display, in the graphical representation, a visual indicator of the relative peripheral control of the working tissue flow with respect to the value or range of the corresponding relative peripheral control of working tissue flow for the desired fitness or health objective;

receiving an update to the working tissue flow and the relative peripheral control; and causing to display, in the graphical user interface, an adjusted position of the visual indicator of the working tissue flow and the relative peripheral control in relation to the corresponding value or range for the relative peripheral control of working tissue flow for the desired fitness or health objective based on the update.

10. The method of claim 9, further comprising:
determining an updated working tissue flow of the subject upon receiving at least one updated measure from a tracker device.

11. The method of claim 10, wherein determining the working tissue flow of the subject comprises using at least a stiffness index (SI), a local dilation response (LD), and an autonomic constriction index (AC) of the subject, and
wherein determining the updated working tissue flow of the subject comprises:
regenerating at least one of the SI, the LD, or the AC of the subject using the at least one updated measure to generate an updated SI, LD, or AC and recalculating the working tissue flow with the updated SI, LD, or AC and a prior SI, LD, or AC that was not regenerated due to receiving the updated measure.

12. The method of claim 9, further comprising determining the value indicative of the of the resistance in the vessel bed of the subject using a stiffness index (SI), a local dilation response (LD), and an autonomic constriction index (AC) by:
calculating a CAFICH score using CAFICH score=[(LD/AC)+(1/SI)] with optional scaling factors,
wherein the resistance in the vessel bed is proportional to the reciprocal of the CAFICH score, wherein the CAFICH score is used to identify the relative peripheral control.

* * * * *